United States Patent
Schutz et al.

(10) Patent No.: US 10,214,775 B2
(45) Date of Patent: Feb. 26, 2019

(54) PROSTATE CANCER ASSOCIATED CIRCULATING NUCLEIC ACID BIOMARKERS

(71) Applicant: CHRONIX BIOMEDICAL, San Jose, CA (US)

(72) Inventors: Ekkehard Schutz, Gottingen (DE); Julia Beck, Gottingen (DE); Howard Urnovitz, San Jose, CA (US)

(73) Assignee: Chronix Biomedical, San Jose, CA (US)

(*) Notice: Subject to any disclaimer, the term of this patent is extended or adjusted under 35 U.S.C. 154(b) by 687 days.

(21) Appl. No.: 14/414,882

(22) PCT Filed: Dec. 7, 2012

(86) PCT No.: PCT/US2012/068489
§ 371 (c)(1),
(2) Date: Jan. 14, 2015

(87) PCT Pub. No.: WO2013/086352
PCT Pub. Date: Jun. 13, 2013

(65) Prior Publication Data
US 2015/0167069 A1    Jun. 18, 2015

Related U.S. Application Data

(60) Provisional application No. 61/568,065, filed on Dec. 7, 2011.

(51) Int. Cl.
*C12Q 1/6869* (2018.01)
*C12Q 1/6886* (2018.01)

(52) U.S. Cl.
CPC ........ *C12Q 1/6869* (2013.01); *C12Q 1/6886* (2013.01)

(58) Field of Classification Search
None
See application file for complete search history.

(56) References Cited

U.S. PATENT DOCUMENTS

2010/0112575 A1    5/2010   Fan et al.

FOREIGN PATENT DOCUMENTS

| WO | 2008/143993 A2 | 11/2008 |
| WO | 2008/153804 A2 | 12/2008 |
| WO | 2011/130751 A1 | 10/2011 |

OTHER PUBLICATIONS

Schwarzenbach, Heidi, et al. "Cell-free tumor DNA in blood plasma as a marker for circulating tumor cells in prostate cancer." Clinical Cancer Research 15.3 (2009): 1032-1038.*
International Search Report and Written Opinion dated Mar. 15, 2013 of International Patent Application No. PCT/US2012/068489, 13 pages.

* cited by examiner

*Primary Examiner* — G Steven Vanni
(74) *Attorney, Agent, or Firm* — Kilpatrick Townsend & Stockton, LLP

(57) ABSTRACT

The invention provides methods and reagents for diagnosing prostate cancer that are based on the detection of biomarkers in the circulating nucleic acids from a patient to be evaluated.

6 Claims, 5 Drawing Sheets

US 10,214,775 B2

PROSTATE CANCER ASSOCIATED CIRCULATING NUCLEIC ACID BIOMARKERS

CROSS-REFERENCES TO RELATED APPLICATIONS

This application is a National Stage of International Application No. PCT/US2012/068489, filed Dec. 7, 2012, and which claims priority benefit of U.S. provisional application no. 61/568,065 filed Dec. 7, 2011, which is herein incorporated by reference for all purposes.

BACKGROUND OF THE INVENTION

Methods to detect prostate cancer, including PSA tests, are extremely unreliable (see, e.g., Wever et al., *J Natl Cancer Inst* 2010; 102:352-355, 2010; Schröder et al., *N. Engl. J. Med* 360:1320-1328, 2009). There is a need for effective detection methods. This invention addresses that need.

BRIEF SUMMARY OF THE INVENTION

The invention is based, in part, on the discovery of cell-free circulating nucleic acids (CNA) biomarkers associated with prostate cancer. In some embodiments, the CNA biomarkers are nucleic acid sequences, in the current invention DNA sequences, that are present in the blood, e.g., in a serum or plasma sample, of a prostate cancer patient, but are rarely present, if at all, in the blood, e.g., a serum or plasma sample, obtained from a normal individual, i.e., in the context of this invention, an individual that does not have prostate cancer. In some embodiments, the CNA biomarkers are nucleic acid sequences, in the current invention DNA sequences, i.e., DNA fragments, that are present in the blood, e.g., in a serum or plasma sample, of a normal individual, but are rarely present, if at all, in the blood, e.g., a serum or plasma sample, obtained from a prostate cancer patient.

Accordingly, in one aspect, the invention provides a method of analyzing CNA in a sample (blood, serum or plasma) from a patient comprising detecting the presence of at least one cell-free DNA having a nucleotide sequence falling within a chromosomal region set forth in Table 1 or Table 4 in the sample. In some embodiments, detecting the level of the at least one biomarker comprises detecting a cell-free DNA molecule having between at least 20 to at least 500 consecutive nucleotides, or, e.g., between at least 50 and at least 400 consecutive nucleotides of a unique sequence within a chromosomal region as set forth in Table 1. In some embodiments, the chromosomal regions is set forth in Table 4.

In one embodiment, a method of analyzing circulating free DNA in a patient sample is provided, comprising determining, in a sample that is blood, serum or plasma, the presence or absence, or the amount of, at least 2, 3, 4, 5, 7, 8, 9, 10, 11, 12, 13, 14, 15, 16, 17, 18, 19, 20, 21, 22, 23, 24, 25, 26, 27, 28, 29, 30, 40, 45, 50, 55, 60, 65, 70, 75, 80, 85, 90, 95 or 100 cell-free DNA molecules each having a sequence falling within a different chromosomal region set forth in Table 1 or Table 4, and preferably the sequences of the cell-free DNA molecules are free of repetitive element. In preferred embodiments, the cell-free DNA molecules have sequences falling within different chromosomal regions in the same table selected from Table 1 or Table 4.

In another aspect, the present invention provides a kit including two or more (e.g., at least 2, 3, 4, 5, 7, 8, 9, 10, 11, 12, 13, 14, 15, 16, 17, 18, 19, 20, 21, 22, 23, 24, 25, 26, 27, 28, 29, 30, 40, 45, 50, 55, 60, 65, 70, 75, 80, 85, 90, 95 or 100) sets of oligonucleotides. In some embodiments, the kit includes 100 or fewer sets of oligonucleotides. Each set comprises one or more oligonucleotides with a nucleotide sequence falling within one single chromosomal region that is set forth in Table 1 or Table 4. Preferably, different oligonucleotide sets correspond to different chromosomal regions within the same table selected from Table 1 or Table 4. Also, preferably the oligonucleotides are free of repetitive element. Optionally, the oligonucleotides are attached to one or more solid substrates such as microchips and beads.

In another aspect, the present invention provides a method of diagnosing or screening for prostate cancer in a patient. The method includes the steps of: (a) determining, in a sample that is blood, serum or plasma from a patient, the presence or absence or the amount of, at least 2, 3, 4, 5, 7, 8, 9, 10, 11, 12, 13, 14, 15, 16, 17, 18, 19, 20, 21, 22, 23, 24, 25, 26, 27, 28, 29, 30, 40, 45, 50, 55, 60, 65, 70, 75, 80, 85, 90, 95 or 100 cell-free DNA molecules each having a sequence falling within a different chromosomal region set forth in Table 1 or Table 4, and (b) correlating the presence of, or an increased amount of, said first and second cell-free DNAs with an increased likelihood that the patient has prostate cancer. Preferably, the sequences of the cell-free DNA molecules are free of repetitive elements. In preferred embodiments, the cell-free DNA molecules have sequences falling within different chromosomal regions in the same table chosen from Table 1 or Table 4.

In one aspect, the invention provides a method of identifying a patient that has a CNA biomarker associated with prostate cancer, the method comprising detecting an increase in the level, relative to normal, of at least one biomarker designated as "UP" in Table 1 or Table 4, in a CNA sample obtained from serum or plasma from the patient. A biomarker can be identified using any number of methods, including sequencing of CNA as well as use of a probe or probe set to detect the presence of the biomarker.

In some embodiments, the invention provides a method of identifying a patient that has a CNA biomarker associated with prostate cancer, the method comprising detecting a decrease in the level, relative to normal, of at least one biomarker designated as "DOWN" in Table 1 or Table 4 in CNA sample from serum or plasma from the patient. A biomarker can be identified using any number of methods, including sequencing of CNA as well as use of a probe or probe set to detect the presence of the biomarker.

In a further aspect, the invention provides a kit for identifying a patient that has a biomarker for prostate cancer and/or that has a biomarker associated with a normal individual that does not have prostate cancer, wherein the kit comprises at least one polynucleotide probe to a biomarker set forth in Table 1 or Table 4. Preferably, such a kit comprises probes to multiple biomarkers, e.g., at least 2, 3, 4, 5, 7, 8, 9, 10, 11, 12, 13, 14, 15, 16, 17, 18, 19, 20, 21, 22, 23, 24, 25, 26, 27, 28, 29, 30, 40, 45, 50, 55, 60, 65, 70, 75, 80, 85, 90, 95 or 100, of the biomarkers set forth in Table 1 or Table 4. In some embodiments, the cell-free DNA molecules have a sequence falling within a different chromosomal region set forth in Table 1 or Table 4. In some embodiments, the kit also includes an electronic device or computer software to compare the hybridization patterns of the CNA in the patient sample to a prostate cancer data set comprising a listing of biomarkers that are present in prostate cancer patient CNA, but not CNA samples from normal individuals.

In some embodiments, the presence of the at least one biomarker in CNA is determined by sequencing. In some embodiments, the presence of the at least one biomarker in CNA is determined using an array. In some embodiments, the presence of the at least one biomarker in CNA is determined using an assay that comprises an amplification reaction, such as a polymerase chain reaction (PCR). In some embodiments, a nucleic acid array forming a probe set comprising probes to two or more chromosomal regions set forth in Table 1 or Table 4 is employed. In some embodiments, a nucleic acid array forming a probe set comprising 2, 3, 4, 5, 6, 7, 8, 9, 10, 11, 12, 13, 14, 15, 16, 17, 18, 19, 20, 21, 22, 23, 24, 25, 26, or 27 of the chromosomal regions set forth in Table 4 is employed. In some embodiments, a nucleic acid array forming a probe set comprising 2, 3, 4, 5, 6, 7, 8, 9, 10, 15, 20, 25, 30, 35, 40, 45, 50, 55, 60, 65, 70, 75, 80, 85, 90, 95, or 100 of the chromosomal regions set forth in Table 1 is employed.

In an additional aspect, the invention provides a method of detecting prostate cancer in a patient that has, or is suspected of having, prostate cancer, the method comprising contacting DNA from the serum or plasma sample with a probe that selectively hybridizes to a sequence present on a chromosomal region described herein, e.g., a sequence set forth in Table 1 or Table 4 under conditions in which the probe selectively hybridizes to the sequence; and detecting the presence or absence of hybridization of the probe, wherein the level of hybridization to the sequence is indicative of prostate cancer.

DETAILED DESCRIPTION OF THE INVENTION

Figure 1:
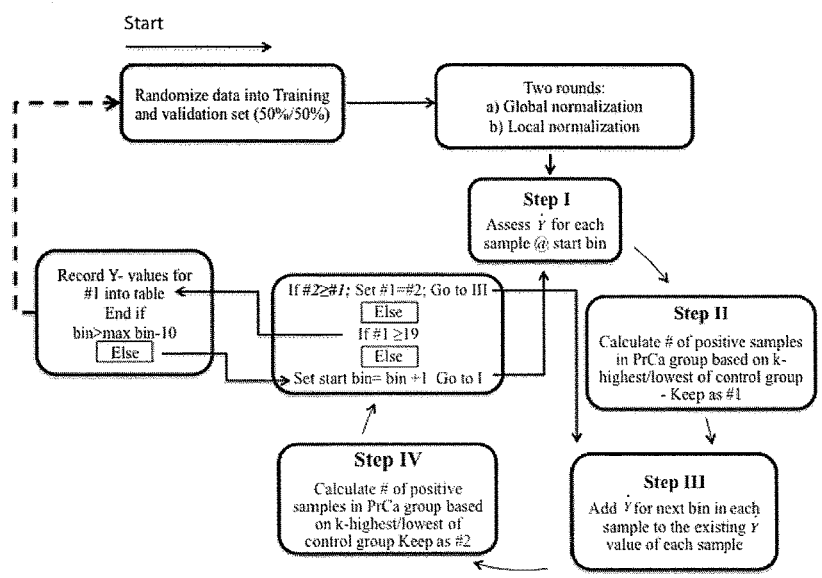
FIG. 1 illustrates the flowchart of unsupervised cluster search (UCS) methodology.
Figure 2:
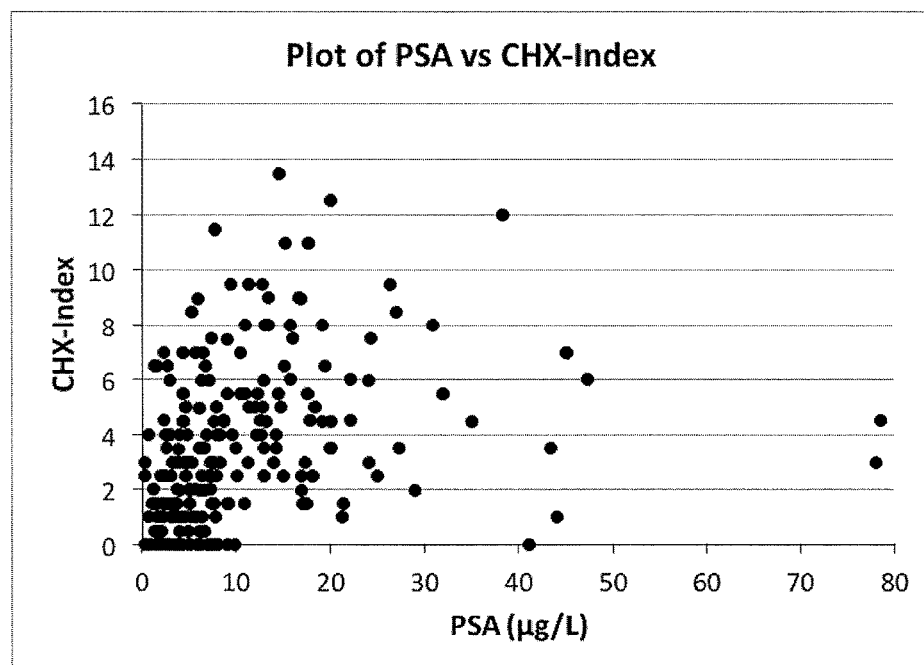
FIG. 2 shows a correlation of a chromosomal region biomarker and PSA test.

As used herein, a "biomarker" refers to a nucleic acid sequence that corresponds to a chromosomal region, where the level of the nucleic acid in CNA relative to normal is associated with prostate cancer. In some embodiments, in which a biomarker is indicated as "UP" in Table 1 or Table 4, the level in CNA of a prostate cancer patient is increased relative to normal. In some embodiments, in which a biomarker is indicated as "DOWN" in Table 1 or Table 4, the level in CNA of a prostate cancer patient is decreased relative to normal.

In the current invention, a "chromosomal region" listed in Table 1 or Table 4 refers to the region of the chromosome that corresponds to the nucleotide positions indicated in the tables. The nucleotide positions on the chromosomes are numbered according to *Homo sapiens* (human) genome, hg18/build 36.1 genome version release March 2006. As understood in the art, there are naturally occurring polymorphisms in the genome of individuals. Thus, each chromosome region listed in Table 1 or Table 4 encompasses allelic variants as well as the particular sequence in the database. An allelic variant typically has at least 95% identity, often at least 96%, at least 97%, at least 98%, or at least 99% identity to the sequence of a chromosomal region that is present in a particular database, e.g., the National Center for Biotechnology Information (*Homo sapiens* Build 36.1 at the website address www.ncbi.nlm.nih.gov/mapview/.) Percent identity can be determined using well known algorithms, including the BLAST algorithm, e.g., set to the default parameters. Further, it is understood that the nucleotide sequences of the chromosomes may be improved upon as errors in the current database are discovered and corrected. The term "chromosomal region" encompasses any variant or corrected version of the same region as defined in Table 1 or Table 4. Given the information provided in Table 1 or Table 4 in the present disclosure and the available genome databases, a skilled person in the art will be able to understand the chromosomal regions used for the present invention even after new variants are discovered or errors are corrected.

"Detecting a chromosomal region" in CNA in the context of this invention refers to detecting the level of any sequence from a chromosomal region shown in Table 1 or Table 4, where the sequence detected can be assigned unambiguously to that chromosomal region. Thus, this term refers to the detection of unique sequences from the chromosomal regions. In the current invention, the level of at least one region, typically multiple regions used in combination, in a CNA sample is compared to the range found for such region in a group of "normal" individuals, i.e., in the context of this invention, individuals who do not have cancer or at least have not been diagnosed with cancer. For regions that are increased in level in prostate cancer patients, i.e., regions listed as UP in Table 1 or Table 4, a result is typically considered to be increased if the result for the sample is higher than the 60th, 70th, 75th, 80th, 85th, 90th, 95th, or 99th percentile. For regions that are decreased in level in prostate cancer patients, i.e., regions listed as DOWN in Table 1 or Table 4, a result is typically considered to be decreased if the result for the sample is below the 40th, 30th, 25th, 20th, 15th, 10th, 5th, or 1st percentile in normal individuals. Methods of removing repetitive sequences from the analysis are known in the art and include use of blocking DNA, e.g., when the target nucleic acids are identified by hybridization. In some embodiments, typically where the presence of a prostate cancer biomarker is determined by sequencing the CNA from a patient, well known computer programs and manipulations can be used to remove repetitive sequences from the analysis (see, e.g., the EXAMPLES section). In addition, sequences that have multiple equally fitting alignment to the reference database are typically omitted from further analyses.

The term "detecting a biomarker" as used herein refers to detecting a polynucleotide, e.g., DNA, from a chromosomal region listed in Table 1 or Table 4 in CNA. As used herein, "detecting the level" of a biomarker encompasses quantitative measurements as well as detecting the presence, or absence, of the biomarker. Thus, e.g., the term "detecting an increase in the level of" a biomarker, relative to normal, includes qualitative embodiments in which the biomarker is detected in a patient sample, but not a normal sample. Similarly, the term "detecting a decrease in the level of" a biomarker, relative to normal, includes embodiments in which the biomarker is not detected in a patient sample, but is detected in normal samples. A biomarker is considered to be "present" if any nucleic acid sequence in the CNA is unambiguously assigned to the chromosomal region.

The term "unambiguously assigned" in the context of this invention refers to determining that a DNA detected in the CNA of a patient is from a particular chromosomal region. Thus, in detection methods that employ hybridization, the probe hybridizes specifically to that region. In detection methods that employ amplification, the primer(s) hybridizes specifically to that region. In detection methods that employ sequencing, the sequence is assigned to that region based on well-known algorithms for identity, such as the BLAST algorithm using high stringent parameters, such as e<0.0001. In addition, such a sequence does not have a further equally fitting hit on the used database.

The term "circulating nucleic acids" or "CNA" refers to cell-free nucleic acids, i.e., that are not contained with any intact cells in human blood, that are present in the blood.

The term "circulating cell-free DNA" as used herein means free DNA molecules of 25 nucleotides or longer that are not contained within any intact cells in human blood, and can be obtained from human serum or plasma.

The term "hybridization" refers to the formation of a duplex structure by two single stranded nucleic acids due to complementary base pairing. Hybridization can occur between exactly complementary nucleic acid strands or between nucleic acid strands that contain minor regions of mismatch. As used herein, the term "substantially complementary" refers to sequences that are complementary except for minor regions of mismatch. Typically, the total number of mismatched nucleotides over a hybridizing region is not more than 3 nucleotides for sequences about 15 nucleotides in length. Conditions under which only exactly complementary nucleic acid strands will hybridize are referred to as "stringent" or "sequence-specific" hybridization conditions. Stable duplexes of substantially complementary nucleic acids can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs. For example, computer software for calculating duplex stability is commercially available from National Biosciences, Inc. (Plymouth, Minn.); e.g., OLIGO version 5, or from DNA Software (Ann Arbor, Mich.), e.g., Visual OMP 6.

Stringent, sequence-specific hybridization conditions, under which an oligonucleotide will hybridize only to the target sequence, are well known in the art (see, e.g., the general references provided in the section on detecting polymorphisms in nucleic acid sequences). Stringent conditions are sequence-dependent and will be different in different circumstances. Generally, stringent conditions are selected to be about 5° C. lower to 5° C. higher than the thermal melting point (Tm) for the specific sequence at a defined ionic strength and pH. The Tm is the temperature (under defined ionic strength and pH) at which 50% of the duplex strands have dissociated. Relaxing the stringency of the hybridizing conditions will allow sequence mismatches to be tolerated; the degree of mismatch tolerated can be controlled by suitable adjustment of the hybridization conditions.

The term "primer" refers to an oligonucleotide that acts as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The primer includes a "hybridizing region" exactly or substantially complementary to the target sequence, preferably about 15 to about 35 nucleotides in length. A primer oligonucleotide can either consist entirely of the hybridizing region or can contain additional features which allow for the detection, immobilization, or manipulation of the amplified product, but which do not alter the ability of the primer to serve as a starting reagent for DNA synthesis. For example, a nucleic acid sequence tail can be included at the 5' end of the primer that hybridizes to a capture oligonucleotide.

The term "probe" refers to an oligonucleotide that selectively hybridizes to a target nucleic acid under suitable conditions. A probe for detection of the biomarker sequences described herein can be any length, e.g., from 15-500 bp in length. Typically, in probe-based assays, hybridization probes that are less than 50 bp are preferred.

The term "target sequence" or "target region" refers to a region of a nucleic acid that is to be analyzed and comprises the sequence of interest.

As used herein, the terms "nucleic acid," "polynucleotide" and "oligonucleotide" refer to primers, probes, and oligomer fragments. The terms are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded DNA, as well as double- and single-stranded RNA. Oligonucleotides for use in the invention may be used as primers and/or probes.

A nucleic acid, polynucleotide or oligonucleotide can comprise phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases. These bases may serve a number of purposes, e.g., to stabilize or destabilize hybridization; to promote or inhibit probe degradation; or as attachment points for detectable moieties or quencher moieties. For example, a polynucleotide of the invention can contain one or more modified, non-standard, or derivatized base moieties, including, but not limited to, N6-methyladenine, N6-tert-butyl-benzyl-adenine, imidazole, substituted imidazoles, 5-fluorouracil, 5 bromouracil, 5-chlorouracil, 5-iodouracil, hypoxanthine, xanthine, 4-acetylcytosine, 5 (carboxyhydroxymethyl)uracil, 5 carboxymethylaminomethyl-2-thiouridine, 5 carboxymethylaminomethyluracil, dihydrouracil, beta-D-galactosylqueosine, inosine, N6 isopentenyladenine, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2 thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine. Other examples of modified, non-standard, or derivatized base moieties may be found in U.S. Pat. Nos. 6,001,611; 5,955,589; 5,844,106; 5,789,562; 5,750,343; 5,728,525; and 5,679,785, each of which is incorporated herein by reference in its entirety. Furthermore, a nucleic acid, polynucleotide or oligonucleotide can comprise one or more modified sugar moieties including, but not limited to, arabinose, 2-fluoro-arabinose, xylulose, and a hexose.

The term "repetitive element" as used herein refers to a stretch of DNA sequence of at least 25 nucleotides in length that is present in the human genome in at least 50 copies.

The terms "arrays," "microarrays," and "DNA chips" are used herein interchangeably to refer to an array of distinct polynucleotides affixed to a substrate, such as glass, plastic, paper, nylon or other type of membrane, filter, chip, bead, or any other suitable solid support. The polynucleotides can be synthesized directly on the substrate, or synthesized separate from the substrate and then affixed to the substrate. The arrays are prepared using known methods.

Introduction

The invention is based, at least in part, on the identification CNA sequences from particular chromosomal regions that are present or at an increased amount in the blood of patients that have prostate cancer, but are rarely, if ever, present, or at a lower amount, in the blood of normal patients that do not have prostate cancer. The invention is also based, in part, on the identification of biomarkers in the CNA in normal individuals, i.e., in the context of this invention, individuals not diagnosed with prostate cancer, that are rarely, if ever, present in patients with prostate cancer. Thus, the invention provides methods and devices for analyzing for the presence of sequences from a chromosomal region corresponding to at least one of the chromosomal regions set forth in Table 1 or Table 4.

Accordingly, in one aspect, the invention provides a method of analyzing CNA in a sample (blood, serum or plasma) from a patient comprising detecting the presence of, or an amount of, at least one circulating cell-free DNA having a nucleotide sequence of at least 25 nucleotides falling within a chromosomal region set forth in Table 1. In some embodiments, the invention provides a method of analyzing CNA in a sample (blood, serum or plasma) from a patient comprising detecting the presence of, or an amount of, at least one circulating cell-free DNA having a nucleotide sequence of at least 25 nucleotides falling within a chromosomal region set forth in Table 4. Preferably, the circulating cell-free DNA is free of repetitive element. In one embodiment, the patient is an individual suspected of or diagnosed with cancer, e.g., prostate cancer.

By "falling within" it is meant herein that the nucleotide sequence of a circulating cell-free DNA is substantially identical (e.g., greater than 95% identical) to a part of the nucleotide sequence of a chromosome region. In other words, the circulating cell-free DNA can hybridize to under stringent conditions, or be derived from, the chromosomal region.

In one embodiment, a method of analyzing circulating cell-free DNA in a patient sample is provided, comprising determining, in a sample that is blood, serum or plasma, the presence or the amount of, a plurality of circulating cell-free DNA molecules each having a sequence of at least 25 nucleotides in length, or at least 40, 50, 60, 75, or 100 or more consecutive nucleotides falling within the same one single chromosomal region set forth in Table 1 or Table 4. There may be two or more or any number of different circulating cell-free DNA molecules that are all derived from the same one chromosomal region set forth in Table 1 or Table 4, and in some embodiments, all such circulating cell-free DNA molecules are detected and/or the amounts thereof are determined.

Preferably the sequences of the circulating cell-free DNA molecules are free of repetitive elements.

In one embodiment, a method of analyzing circulating cell-free DNA in a patient sample is provided, comprising determining, in a sample that is blood, serum or plasma, the presence or absence or the amount of, at least 2, 3, 4, 5, 7, 8, 9, 10, 11, 12, 13, 14, 15, 16, 17, 18, 19, 20, 21, 22, 23, 24, 25, 26, 27, 28, 29, 30, 40, 45, 50, 55, 60, 65, 70, 75, 80, 85, 90, 95 or 100 circulating cell-free DNA molecules each having a sequence of at least 25 consecutive nucleotides, or at least 40, 50 60, 75, or 100, or more consecutive nucleotides falling within a different chromosomal region set forth in Table 1. In some embodiments, the cell-free DNA molecules have a sequence falling within a different chromosomal region set forth in Table 4. Preferably the sequences of the circulating cell-free DNA molecules are free of repetitive elements. In preferred embodiments, the cell free DNA molecules have sequences falling within different chromosomal regions in the same table that is chosen from Table 1 or Table 4. In one specific embodiment, the presence or absence or the amounts of, at least 2, 3, 4, 5, 7, 8, 9, 10, 11, 12, 13, 14, 15, 16, 17, 18, 19, 20, 21, 22, 23, 24, 25, 26, 27, 28, 29, 30, 40, 45, 50, 55, 60, 65, 70, 75, 80, 85, 90, 95 or 100, circulating cell-free DNA molecules are determined, the sequence of each falling within a different chromosomal region set forth in Table 1. In some embodiments, the circulating cell-free DNA molecules have a sequence falling within a different chromosomal region set forth in Table 4.

In another specific embodiment, the method of analyzing circulating cell-free DNA includes the steps of: isolating, from blood, serum or plasma sample of a patient, substantially all circulating cell-free DNA molecules having a length of at least 20, 25, 30, 40, 50, 75 or 100 consecutive nucleotides in length, or between 50 and 400 nucleotides in length, and contacting the circulating cell-free DNA molecules to a plurality of oligonucleotides (e.g., on a DNA chip or microarray) to determine if one or more of the circulating cell-free DNA molecules hybridizes to any one of the plurality of oligonucleotide probes under stringent conditions. Each of the oligonucleotide probes has a nucleotide sequence identical to a part of the sequence of a chromosomal region set forth in Table 1. In some embodiments, each of the oligonucleotide probes has a nucleotide sequence identical to a part of the sequence of a chromosomal region set forth in Table 4. Thus, if a circulating DNA molecule hybridizes under stringent conditions to one of the oligonucleotide probes, it indicates that the circulating DNA molecule has a nucleotide sequence falling within a chromosomal region set forth in Table 1 or Table 4, and indicates the presence of the circulating DNA molecule. The level of the circulating DNA molecule can be determined by determining the amount of hybridized probe(s).

In the above various embodiments, preferably the circulating cell-free DNA molecules have at least 25 consecutive nucleotides in length (preferably at least 50, 70, 80, 100, 120 or 200 consecutive nucleotides in length). More preferably, the circulating cell-free DNA molecules have between about 50 and about 300 or 400, preferably from about 75 and about 300 or 400, more preferably from about 100 to about 200 consecutive nucleotides of a unique sequence within a chromosomal region as set forth in Table 1 or Table 4.

In another aspect, the present invention provides a method of diagnosing or screening for prostate cancer in a patient. The method includes the steps of: (a) determining, in a sample that is blood, serum or plasma from a patient, the level of at least 1, 2, 3, 4, 5, 6, 7, 8, 9, 10, 15, 20, 25, 30, 35, 40, 45, 50, 55, 60, 61, 62, 63, 64, 65, or 66 circulating cell-free DNA molecules each having a sequence of at least 25 nucleotides in length falling within a different chromosomal region designated as "UP" in Table 1, and (b) correlating the presence of an increased level of the circulating cell-free DNAs, relative to normal, with an increased likelihood that the patient has prostate cancer.

In another aspect, the method includes the steps of: (a) determining, in a sample that is blood, serum or plasma from a patient, the level of at least 1, 2, 3, 4, 5, 6, 7, 8, 9, 10, 15, 16, 17, 18, 19, or 20, circulating cell-free DNA molecules each having a sequence of at least 25 nucleotides in length falling within a different chromosomal region designated as "UP" in Table 4, and (b) correlating the presence of an increased level of the circulating cell-free DNAs, relative to normal, with an increased likelihood that the patient has prostate cancer.

In another embodiment, the method of invention includes the steps of: (a) determining, in a sample that is blood, serum or plasma from a patient, the level of at least 1, 2, 3, 4, 5, 6, 7, 8, 9, 10, 15, 20, 25, 30, 31, 32, 33, or 34, circulating cell-free DNA molecules each having a sequence of at least 25 nucleotides in length falling within a different chromosomal region designated as "DOWN" in Table 1; and (b) correlating the presence of a decreased level of the circulating cell-free DNAs, relative to normal, with an increased likelihood that the patient has prostate cancer. In some embodiments, the method of invention includes the steps of: (a) determining, in a sample that is blood, serum or plasma from a patient, the level of at least 1, 2, 3, 4, 5, 6, or 7 circulating cell-free DNA molecules each having a sequence of at least 25 nucleotides in length falling within a different chromosomal region designated as "DOWN" in Table 4; and (b) correlating the presence of a decreased level of the circulating cell-free DNAs, relative to normal, with an increased likelihood that the patient has prostate cancer.

When the steps of the above methods are applied to a patient diagnosed of cancer, the patient may be monitored for the status of prostate cancer, or for determining the treatment effect of a particular treatment regimen, or detecting cancer recurrence or relapse.

When the steps of the above methods are applied to a patient diagnosed with prostate cancer, the patient may be monitored for the status of prostate cancer, or for determining the treatment effect of a particular treatment regimen, or detecting cancer recurrence or relapse.

In the diagnosis/monitoring method of the present invention, preferably the sequences of the circulating cell-free DNA molecules are free of repetitive elements. In preferred embodiments, the cell-free DNA molecules have sequences falling within different chromosomal regions in set forth in Table 1 or Table 4.

In one embodiment, a method of diagnosing prostate cancer in an individual is provided, comprising (a) determining the levels of at least 1, 2, 3, 4, 5, 6, 7, 8, 9, 10, 15, 20, 25, 30, 35, 40, 45, 50, 55, 60, 61, 62, 63, 64, 65, or 66, circulating cell-free DNA molecules each having a sequence of at least 25 nucleotides in length falling within a different chromosomal region designated as "UP" in Table 1; and (b) correlating the presence of an increased level, relative to normal, of one or more of the circulating cell-free DNA molecules with an increased likelihood that the individual has prostate cancer or a recurrence of prostate cancer or a failure of treatment for prostate cancer.

In one embodiment, a method of diagnosing/monitoring prostate cancer in an individual is provided, comprising (a) determining the levels of at least 1, 2, 3, 4, 5, 6, 7, 8, 9, 10, 15, 20, 25, 30, 31, 32, 33, or 34 circulating cell-free DNA molecules each having a sequence of at least 25 nucleotides in length falling within a different chromosomal region designated as "DOWN" in Table 1; and (b) correlating the presence of a decreased level, relative to normal, of one or more of the circulating cell-free DNA molecules with an increased likelihood that the individual has prostate cancer or a recurrence of prostate cancer or a failure of treatment for prostate cancer.

In another embodiment, a method of diagnosing prostate cancer in an individual is provided, comprising (a) determining the levels of at least 1, 2, 3, 4, 5, 6, 7, 8, 9, 10, 15, 16, 17, 18, 19, or 20 circulating cell-free DNA molecules each having a sequence of at least 25 nucleotides in length falling within a different chromosomal region designated as "UP" in Table 4; and (b) correlating the presence of an increased level, relative to normal, of one or more of the circulating cell-free DNA molecules with an increased likelihood that the individual has prostate cancer or a recurrence of prostate cancer or a failure of treatment for prostate cancer.

In another embodiment, a method of diagnosing/monitoring prostate cancer in an individual is provided, comprising (a) determining the levels of at least 1, 2, 3, 4, 5, 6, or 7 circulating cell-free DNA molecules each having a sequence of at least 25 nucleotides in length falling within a different chromosomal region designated as "DOWN" in Table 4; and (b) correlating the presence of a decreased level, relative to normal, of one or more of the circulating cell-free DNA molecules with an increased likelihood that the individual has prostate cancer or a recurrence of prostate cancer or a failure of treatment for prostate cancer.

In yet another embodiment, the method of diagnosing, monitoring or screening for prostate cancer in a patient, includes determining, in a sample that is blood, serum or plasma from the patient, the level of each and all circulating cell-free DNAs, each having a sequence falling within the same one single chromosomal region designated as "UP" in Table 1 or Table 4; and correlating an increased total level of said circulating cell-free DNAs, with an increased likelihood that said patient has prostate cancer, or recurrence of prostate cancer. In other words, there can be any number of and typically many, different circulating cell-free DNA molecules derived from one single same chromosomal region set forth in Table 1 or Table 4, and all of such different circulating cell-free DNA molecules.

In another embodiment, the method of diagnosing, monitoring or screening for prostate cancer in a patient, includes determining, in a sample that is blood, serum or plasma from the patient, the level of each and all circulating cell-free DNAs, each having a sequence falling within the same one single chromosomal region designated as "DOWN" in Table 1 or Table 4; and correlating a decreased level of said circulating cell-free DNAs with an increased likelihood that said patient has prostate cancer, or recurrence of prostate cancer. In other words, there can be any number of, and typically many, different circulating cell-free DNA molecules derived from one single same chromosomal region set forth in Table 1 or Table 4, and all of such different circulating cell-free DNA molecules are detected and the level determined, and correlation with the status of prostate cancer is made.

In a specific embodiment, substantially all circulating cell-free DNA molecules having a length of at least 20, 25, 30, 40, 50, 75 or 100 consecutive nucleotides in length, or between 50 and 400 nucleotides in length, are isolated from a blood, serum or plasma sample of a patient. The sequence of at least some representative portion of each of the isolated circulating cell-free DNA molecules is determined, and compared with one or more of the sequences of the chromosomal regions set forth in Table 1 to determine whether the sequence of a circulating cell-free DNA falls within a chromosomal region designated as "UP" in Table 1 or Table 4, and the level of the circulating DNA having said sequence. If the level is increased relative to normal, a diagnosis of prostate cancer is made. In the case of a patient treated with a therapy for prostate cancer, recurrence is indicated if an increase, relative to normal, in the level of a circulating cell-free DNA that falls within a chromosomal region designated as "UP" in Table 1 or Table 4 is detected. In preferred embodiments, a diagnosis of prostate cancer or prostate cancer treatment failure or recurrence is indicated if two or more circulating cell-free DNA molecules that fall within 2, 3, 4, 5, 6, 7, 8, 9, 10, 15, 20, 25, 30, 35, 40, 45, 50, 55, 60, 65, 66 or more chromosomal regions designated as "UP" in Table 1 are increased. In more preferred embodiments, a diagnosis of prostate cancer or prostate cancer treatment failure or recurrence is indicated if two or more circulating cell-free DNA molecules that fall within 2, 3, 4, 5, 6, 7, 8, 9, 10, 15, 20, or more chromosomal regions designated as "UP" in Table 4 are increased.

In another specific embodiment, substantially all circulating cell-free DNA molecules having a length of at least 20, 25, 30, 40, 50, 75 or 100 consecutive nucleotides in length, or between 50 and 400 nucleotides in length, are isolated from a blood, serum or plasma sample of a patient. These circulating cell-free DNA molecules, or a representative portion thereof, are hybridized to a microarray that is described above in the context of the kit invention to determine if one of the circulating cell-free DNA molecules hybridizes to any one of a plurality of oligonucleotide probes under stringent conditions. Each of the oligonucleotide probes has a nucleotide sequence identical to a part of the sequence of a chromosomal region designated as "UP" in Table 1 or Table 4. Thus, if a circulating DNA molecule hybridizes under stringent conditions to one of the oligonucleotide probes, it indicates that the circulating DNA molecule has a nucleotide sequence falling within a chromosomal region set forth in Table 1 or Table 4, and the level is determined. If the level is increased, relative to normal, a diagnosis of prostate cancer is made. In the case of a patient treated with a therapy for prostate cancer, recurrence is indicated if there is an increase in the level of a circulating cell-free DNA falls within a chromosomal region designated as "UP" in Table 1 is detected. In preferred embodiments, a diagnosis of prostate cancer or prostate cancer treatment failure or recurrence is indicated if two or more circulating cell-free DNA molecules fall within 2, 3, 4, 5, 6, 7, 8, 9, 10, 15, 20, 25, 30, 35, 40, 45, 50, 55, 60, 65, 66 or more chromosomal regions designated as "UP" in Table 1 are increased. In more preferred embodiments, a diagnosis of prostate cancer or prostate cancer treatment failure or recurrence is indicated if two or more circulating cell-free DNA molecules fall within 2, 3, 4, 5, 6, 7, 8, 9, 10, 11, 12, 13, 14, 15, 16, 17, 18, 19, 20 or more chromosomal regions designated as "UP" in Table 4 are increased.

In a specific embodiment, substantially all circulating cell-free DNA molecules having a length of at least 20, 25, 30, 40, 50, 75 or 100 consecutive nucleotides in length, or between 50 and 400 nucleotides in length, are isolated from a blood, serum or plasma sample of a patient. The sequence of at least some representative portion of each of the isolated circulating cell-free DNA molecules is determined, and compared with one or more of the sequences of the chromosomal regions set forth in Table 1 or Table 4 to determine whether the sequence of a circulating cell-free DNA falls within a chromosomal region designated as "DOWN" in Table 1 or Table 4 and the level of the polynucleotide having said sequence. If the level is decreased relative to normal, a diagnosis of prostate cancer is made. In the case of a patient treated with a therapy for prostate cancer, recurrence is indicated if a decrease, relative to normal, in the level of a circulating cell-free DNA that falls within a chromosomal region designated as "DOWN" in Table 1 or Table 4 is detected. In preferred embodiments, a diagnosis of prostate cancer or prostate cancer treatment failure or recurrence is indicated if two or more circulating cell-free DNA molecules that fall within 2, 3, 4, 5, 6, 7, 8, 9, 10, or more chromosomal regions designated as "DOWN" in Table 1 are decreased. In more preferred embodiments, a diagnosis of prostate cancer or prostate cancer treatment failure or recurrence is indicated if two or more circulating cell-free DNA molecules that fall within 2, 3, 4, 5, 6, 7, or more chromosomal regions designated as "DOWN" in Table 4 are decreased.

In another specific embodiment, substantially all circulating cell-free DNA molecules having a length of at least 20, 25, 30, 40, 50, 75 or 100 consecutive nucleotides in length, or between 50 and 400 nucleotides in length, are isolated from a blood, serum or plasma sample of a patient. These circulating cell-free DNA molecules, or a representative portion thereof, are hybridized to a microarray that is described above in the context of the kit invention to determine if one of the circulating cell-free DNA molecules hybridizes to any one of a plurality of oligonucleotide probes under stringent conditions. Each of the oligonucleotide probes has a nucleotide sequence identical to a part of the sequence of a chromosomal region designated as "DOWN" in Table 1 or Table 4. Thus, if a circulating DNA molecule hybridizes under stringent conditions to one of the oligonucleotide probes, it indicates that the circulating DNA molecule has a nucleotide sequence falling within a chromosomal region set forth in Table 1 or Table 4, and the level is determined. If the level is decreased, relative to normal, a diagnosis of prostate cancer is made. In the case of a patient treated with a therapy for prostate cancer, recurrence is indicated if there is a decrease in the level of a circulating cell-free DNA falls within a chromosomal region designated as "DOWN" in Table 1 or Table 4 is detected. In preferred embodiments, a diagnosis of prostate cancer or prostate cancer treatment failure or recurrence is indicated if two or more circulating cell-free DNA molecules fall within 2, 3, 4, 5, 6, 7, 8, 9, 10, or more chromosomal regions designated as "DOWN" in Table 1 are decreased. In more preferred embodiments, a diagnosis of prostate cancer or prostate cancer treatment failure or recurrence is indicated if two or more circulating cell-free DNA molecules fall within 2, 3, 4, 5, 6, or 7 chromosomal regions designated as "DOWN" in Table 4 are decreased.

In the above various embodiments, preferably the circulating cell-free DNA molecules have at least 25 consecutive nucleotides in length (preferably at least 50, 70, 80, 100, 120 or 200 consecutive nucleotides in length). More preferably, the circulating cell-free DNA molecules have between about 50 and about 300 or 400, preferably from about 75 and about 300 or 400, more preferably from about 100 to about 200 consecutive nucleotides of a unique sequence within a chromosomal region as set forth in Table 1 or Table 4.

Detection of Circulating Nucleic Acids in the Blood

In order to detect the presence of circulating nucleic acids in the blood of patients that may have, or are suspected of having, prostate cancer, a blood sample is obtained from the patient. Serum or plasma from the blood sample is then analyzed for the presence of a circulating cell-free DNA or biomarker as described herein. Nucleic acids can be isolated from serum or plasma using well known techniques, see, e.g., the example sections. In the context of the current invention, the nucleic acid sequences that are analyzed are DNA sequences. Thus, in this section, methods described as evaluating "nucleic acids" refers to the evaluation of DNA.

Detection techniques for evaluating nucleic acids for the presence of a biomarker involve procedures well known in the field of molecular genetics. Further, many of the methods involve amplification of nucleic acids. Ample guidance for performing is provided in the art. Exemplary references include manuals such as PCR Technology: *Principles and Applications for DNA Amplification* (ed. H. A. Erlich, Freeman Press, NY, N.Y., 1992); PCR Protocols: A Guide to Methods and Applications (eds. Innis, et al., Academic Press, San Diego, Calif., 1990); Current Protocols in Molecular Biology, Ausubel, 1994-1999, including supplemental updates through April 2004; Sambrook & Russell, *Molecular Cloning, A Laboratory Manual* (3rd Ed, 2001).

Although the methods may employ PCR steps, other amplification protocols may also be used. Suitable amplification methods include ligase chain reaction (see, e.g., Wu & Wallace, *Genomics* 4:560-569, 1988); strand displacement assay (see, e.g., Walker et al., *Proc. Natl. Acad. Sci. USA* 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., *Proc. Natl. Acad. Sci. USA* 86:1173-1177, 1989); and self-sustained sequence replication (3SR) (Guatelli et al., *Proc. Natl. Acad. Sci. USA* 87:1874-1878, 1990; WO 92/08800). Alternatively, methods that amplify the probe to detectable levels can be used, such as Qβ-replicase amplification (Kramer & Lizardi, *Nature* 339:401-402, 1989; Lomeli et al., *Clin. Chem.* 35:1826-1831, 1989). A review of known amplification methods is provided, for example, by Abramson and Myers in *Current Opinion in Biotechnology* 4:41-47, 1993.

In some embodiments, the detection of biomarker in the CNA of a patient is performed using oligonucleotide primers and/or probes to detect a target sequence, wherein the target sequence is present in (e.g., comprises some unambiguously assigned portion of) any of the chromosomal regions listed in Table 1 or Table 4. Oligonucleotides can be prepared by any suitable method, usually chemical synthesis, and can also be purchased through commercial sources. Oligonucleotides can include modified phosphodiester linkages (e.g., phosphorothioate, methylphosphonates, phosphoamidate, or boranophosphate) or linkages other than a phosphorous acid derivative into an oligonucleotide may be used to prevent cleavage at a selected site. In addition, the use of 2'-amino modified sugars tends to favor displacement over digestion of the oligonucleotide when hybridized to a nucleic acid that is also the template for synthesis of a new nucleic acid strand.

In one embodiment, the biomarker is identified by hybridization under sequence-specific hybridization conditions with a probe that targets a chromosomal region (e.g., targets some unambiguously assigned portion of, any of the chromosomal regions listed in Table 1 or Table 4) described herein. The probe used for this analysis can be a long probe or sets for short oligonucleotide probes, e.g., from about 20 to about 150 nucleotides in length may be employed.

Suitable hybridization formats are well known in the art, including but not limited to, solution phase, solid phase, oligonucleotide array formats, mixed phase, or in situ hybridization assays. In solution (or liquid) phase hybridizations, both the target nucleic acid and the probe or primers are free to interact in the reaction mixture. Techniques such as real-time PCR systems have also been developed that permit analysis, e.g., quantification, of amplified products during a PCR reaction. In this type of reaction, hybridization with a specific oligonucleotide probe occurs during the amplification program to identify the presence of a target nucleic acid. Hybridization of oligonucleotide probes ensure the highest specificity due to thermodynamically controlled two state transition. Examples for this assay formats are fluorescence resonance energy transfer hybridization probes, molecular beacons, molecular scorpions, and exonuclease hybridization probes (e.g., reviewed in Bustin, *J Mol. Endocrin.* 25:169-93, 2000).

Suitable assay formats include array-based formats, described in greater detail below in the "Device" section, where probe is typically immobilized. Alternatively, the target may be immobilized.

In a format where the target is immobilized, amplified target DNA is immobilized on a solid support and the target complex is incubated with the probe under suitable hybridization conditions, unhybridized probe is removed by washing under suitably stringent conditions, and the solid support is monitored for the presence of bound probe. In formats where the probes are immobilized on a solid support, the target DNA is typically labeled, usually during amplification. The immobilized probe is incubated with the amplified target DNA under suitable hybridization conditions, unhybridized target DNA is removed by washing under suitably stringent conditions, and the solid support/probe is monitored for the presence of bound target DNA.

In typical embodiments, multiple probes are immobilized on a solid support and the target chromosomal regions in the CNA from a patient are analyzed using the multiple probes simultaneously. Examples of nucleic acid arrays are described by WO 95/11995.

In an alternative probe-less method, amplified nucleic acid corresponding to a target nucleic acid present in a chromosomal region is performed using nucleic acid primers to the chromosomal region and is detected by monitoring the increase in the total amount of double-stranded DNA in the reaction mixture, is described, e.g., in U.S. Pat. No. 5,994,056; and European Patent Publication Nos. 487,218 and 512,334. The detection of double-stranded target DNA relies on the increased fluorescence various DNA-binding dyes, e.g., SYBR Green, exhibit when bound to double-stranded DNA.

As appreciated by one in the art, specific amplification methods can be performed in reaction that employ multiple primers to target the chromosomal regions such that the biomarker can be adequately covered.

DNA Sequencing

In preferred embodiments, the presence of a sequence from a chromosomal region set forth in Table 1 or Table 4 in the CNA from a patient undergoing evaluation is detected by direct sequencing. Such sequencing, especially using the Roche 454, Illumina, and Applied Biosystems sequencing systems mentioned below or similar advanced sequencing systems, can include quantitation (i.e., determining the level) of nucleic acids having a particular sequence. Such quantitation can be used in the embodiments of the invention that involve determining the level of a biomarker (some embodiments of which involve correlating a particular level to the presence or absence of cancer). Methods include e.g., dideoxy sequencing-based methods although other methods such as Maxam and Gilbert sequencing are also known (see, e.g., Sambrook and Russell, supra). In typical embodiments, CNA from a patient is sequenced using a large-scale sequencing method that provides the ability to obtain sequence information from many reads. Such sequencing platforms includes those commercialized by Roche 454 Life Sciences (GS systems), Illumina (e.g., HiSeq, MiSeq) and Applied Biosystems (e.g., SOLiD systems).

The Roche 454 Life Sciences sequencing platform involves using emulsion PCR and immobilizing DNA fragments onto bead. Incorporation of nucleotides during synthesis is detected by measuring light that is generated when a nucleotide is incorporated.

The Illumina technology involves the attachment of randomly fragmented genomic DNA to a planar, optically transparent surface. Attached DNA fragments are extended and bridge amplified to create an ultra-high density sequencing flow cell with clusters containing copies of the same template. These templates are sequenced using a sequencing-by-synthesis technology that employs reversible terminators with removable fluorescent dyes.

Methods that employ sequencing by hybridization may also be used. Such methods, e.g., used in the ABI SOLiD4+ technology uses a pool of all possible oligonucleotides of a fixed length, labeled according to the sequenced position. Oligonucleotides are annealed and ligated; the preferential ligation by DNA ligase for matching sequences results in a signal informative of the nucleotide at that position.

The sequence can be determined using any other DNA sequencing method including, e.g., methods that use semiconductor technology to detect nucleotides that are incorporated into an extended primer by measuring changes in current that occur when a nucleotide is incorporated (see, e.g., U.S. Patent Application Publication Nos. 20090127589 and 20100035252). Other techniques include direct label-free exonuclease sequencing in which nucleotides cleaved from the nucleic acid are detected by passing through a nanopore (Oxford Nanopore) (Clark et al., *Nature Nanotechnology* 4: 265-270, 2009); and Single Molecule Real Time (SMRT™) DNA sequencing technology (Pacific Biosciences), which is a sequencing-by synthesis technique.

Devices and Kits

In a further aspect, the invention provides diagnostic devices and kits useful for identifying one or more prostate cancer-associated biomarkers in the CNA from a patient where the one or more biomarkers is a sequence corresponding to any of the chromosomal regions set forth in Table 1 and/or Table 4. As will be apparent to skilled artisans, the kit of the present invention is useful in the above-discussed method for analyzing circulating cell-free DNA in a patient sample and in diagnosing, screening or monitoring prostate cancer as described above.

Thus, in one aspect, the present invention provides the use of at least one oligonucleotide for the manufacture of a diagnostic kit useful in diagnosing, screening or monitoring prostate cancer. The nucleotide sequence of the oligonucleotide falls within a chromosomal region set forth in Table 1 or Table 4.

Preferably, the kit of the present invention includes one, two or more (e.g., at least 2, 3, 4, 5, 7, 8, 9, 10, 11, 12, 13, 14, 15, 16, 17, 18, 19, 20, 21, 22, 23, 24, 25, 26, 27, 28, 29, 30, 40, 45, 50, 55, 60, 65, 70, 75, 80, 85, 90, 95 or 100, preferably from one to 100 or from 1 to 27, sets of oligonucleotides. Each set comprises one or more oligonucleotides (e.g., from about one to about 10,000, preferably from 50, 100, 200 or 300 to about 10,000). All of the nucleotide sequences of such one or more oligonucleotides in each set fall within the same one single chromosomal region that is set forth in Table 1. In some embodiments, all of the nucleotide sequences of such one or more oligonucleotides in each set fall within the same one single chromosomal region that is set forth in Table 4. Each oligonucleotide should have from about 18 to 100 nucleotides, or from 20 to about 50 nucleotides, and is capable of hybridizing, under stringent hybridization conditions, to the chromosomal region in which its sequence falls. The oligonucleotides are useful as probes for detecting circulating cell-free DNA molecules derived from the chromosomal regions. Preferably, each set includes a sufficient number of oligonucleotides with sequences mapped to one chromosomal region such that any circulating cell-free DNA molecules derived from the chromosomal region can be detected with the oligonucleotide set. Thus, the number of oligonucleotides required in each set is determined by the total length of unique nucleotide sequence of a particular chromosomal region, as will be apparent to skilled artisans. Such total lengths are indicated in Table 1 and Table 4.

Preferably, in the kit of the present invention, different oligonucleotide sets correspond to different chromosomal regions within the same table. Preferably, the oligonucleotides are free of repetitive element. Optionally, the oligonucleotides are attached to one or more solid substrates such as microchips and beads. In preferred embodiments, the kit is a microarray with the above oligonucleotides.

In one embodiment, the kit of the present invention includes a plurality of oligonucleotide sets capable of hybridizing to the chromosomal regions set forth in the tables. That is, the kit includes oligonucleotide probes corresponding to each and every chromosomal regions set forth in Table 1 or Table 4, such that all circulating cell-free DNA derived from any chromosomal region set forth in Table 1 or Table 4 can be detected using the kit.

Use of the oligonucleotides included in the kit described for the manufacture of the kit useful for diagnosing, screening or monitoring prostate cancer is also contemplated. The manufacturing of such kit should be apparent to a skilled artisan.

In some embodiments, a diagnostic device comprises probes to detect at least 2, 3, 4, 5, 6, 7, 8, 9, 10, 15, 20, 30, 40, 50, 60, 75, 80, 85, 90, 95, or 100 chromosomal regions set forth in Table 1. In other embodiments, a diagnostic device comprises probes to detect at least 2, 3, 4, 5, 6, 7, 8, 9, 10, 15, 20, 21, 22, 23, 24, 25, 26 or 27 chromosomal regions set forth in Table 4. In some embodiments, the present invention provides probes attached to a solid support, such as an array slide or chip, e.g., as described in DNA Microarrays: A Molecular Cloning Manual, 2003, Eds. Bowtell and Sambrook, Cold Spring Harbor Laboratory Press. Construction of such devices are well known in the art, for example as described in US patents and patent Publications U.S. Pat. No. 5,837,832; PCT application WO95/11995; U.S. Pat. No. 5,807,522; U.S. Pat. Nos. 7,157,229, 7,083,975, 6,444,175, 6,375,903, 6,315,958, 6,295,153, and 5,143,854, 2007/0037274, 2007/0140906, 2004/0126757, 2004/0110212, 2004/0110211, 2003/0143550, 2003/0003032, and 2002/0041420. Nucleic acid arrays are also reviewed in the following references: *Biotechnol Annu Rev* 8:85-101 (2002); Sosnowski et al, *Psychiatr Genet* 12(4):181-92 (December 2002); Heller, *Annu Rev Biomed Eng* 4: 129-53 (2002); Kolchinsky et al, *Hum. Mutat* 19(4): 343-60 (April 2002); and McGail et al, Adv Biochem Eng Biotechnol 77:21-42 (2002).

Any number of probes may be implemented in an array. A probe set that hybridizes to different, preferably unique, segments of a chromosomal region may be used where the probe set detects any part of the chromosomal region. Alternatively, a single probe to a chromosomal region may be immobilized to a solid surface. Polynucleotide probe can be synthesized at designated areas (or synthesized separately and then affixed to designated areas) on a substrate, e.g., using a light-directed chemical process. Typical synthetic polynucleotides can be about 15-200 nucleotides in length.

The kit can include multiple biomarker detection reagents, or one or more biomarker detection reagents in combination with one or more other types of elements or components (e.g., other types of biochemical reagents, containers, packages such as packaging intended for commercial sale, substrates to which biomarker detection reagents are attached, electronic hardware components, etc.). Accordingly, the present invention further provides biomarker detection kits and systems, including but not limited to arrays/microarrays of nucleic acid molecules, and beads that contain one or more probes or other detection reagents for detecting one or more biomarkers of the present invention. The kits can optionally include various electronic hardware components; for example, arrays ("DNA chips") and microfluidic systems ("lab-on-a-chip" systems) provided by various manufacturers typically comprise hardware components. Other kits may not include electronic hardware components, but may be comprised of, for example, one or more biomarker detection reagents (along with, optionally, other biochemical reagents) packaged in one or more containers.

Biomarker detection kits/systems may contain, for example, one or more probes, or sets of probes, that hybridize to a nucleic acid molecule present in a chromosomal region set forth in Table 1 or Table 4.

A biomarker detection kit of the present invention may include components that are used to prepare CNA from a blood sample from a patient for the subsequent amplification and/or detection of a biomarker.

Correlating the Presence of Biomarkers with Prostate Cancer

The present invention provides methods and reagents for detecting the presence of a biomarker in CNA from a patient that has prostate cancer or that is being evaluated to determine if the patient may have prostate cancer. In the context of the invention, "detection" or "identification" or "identifying the presence" or "detecting the presence" of a biomarker associated with prostate cancer in a CNA sample from a patient refers to determining any level of the biomarker in the CNA of the patient where the level is greater than a threshold value that distinguishes between prostate cancer and non-prostate cancer CNA samples for a given assay.

In the current invention, for example, the presence of, or increase in the level of, relative to normal, any one of the chromosomal regions (i.e., biomarkers) listed as "UP" in Table 1 or Table 4 is indicative of prostate cancer. As appreciated by one of skill in the art, biomarkers may be employed in analyzing a patient sample where the biomarker has also been observed infrequently in a normal patient in order to increase the sensitivity of the detection. Given the low frequency of occurrence in normal samples relative to the higher frequency of occurrence in prostate cancer, the presence of, or increase in level of, the biomarker in a patient indicates that the patient has a 95% or greater likelihood of having prostate cancer. Thus, for example, arrays can be used to detect the chromosomal regions can include those that identify the chromosomal regions in Table 1 or Table 4.

The biomarkers designated as "UP" in Table 1 or Table 4 are associated with prostate cancer, i.e., they are over-represented in prostate cancer patients compared to individuals not diagnosed with prostate cancer. Thus, the detection of an increase, relative to non-prostate cancer patients, in the level of one or more of the biomarkers designated as "UP" in Table 1 or Table 4 is indicative of prostate cancer, i.e., the patient has an increased probability of having prostate cancer compared to a patient that does not have an increase in the level of the biomarker. In some embodiments, the detection and increase in the level of two or more biomarkers designated as "UP" in Table 1 in the CNA of a patient is indicative of a greater probability for prostate cancer. In other embodiments, the detection and increase in the level of two or more biomarkers designated as "UP" in Table 4 in the CNA of a patient is indicative of a greater probability for prostate cancer. As understood in the art, other criteria, e.g., clinical criteria, etc., are also employed to diagnose prostate cancer in the patient. Accordingly, patients that have a biomarker associated with prostate cancer also undergo other diagnostic procedures.

In some embodiments, one or more biomarkers that are under-represented in prostate cancer may be detected in the CNA of a patient. Thus, for example, a biomarker listed in Table 1 or Table 4 may be detected in a CNA sample from a patient where the detection of the biomarker is indicative of a normal diagnosis, i.e., that the patient does not have prostate cancer.

"Over-represented" or "increased amount" means that the level of one or more circulating cell-free DNAs is higher than normal levels. Generally this means an increase in the level as compared to an index value. Conversely, "under-represented" or "decreased amount" means that the level of one or more particular circulating cell-free DNA molecules is lower than normal levels. Generally this means a decrease in the level as compared to an index value.

In preferred embodiments, the test value representing the level of a particular circulating cell-free DNA is compared to one or more reference values (or index values), and optionally correlated to prostate cancer or cancer recurrence. Optionally, an increased likelihood of prostate cancer is indicated if the test value is greater than the reference value for CNA listed as "UP" in Table 1 or Table 4, or less than the reference value for CNA listed as "DOWN" in Table 1 or Table 4.

In some embodiments, once a patient has been determined to have at least one biomarker listed in Table 1 or Table 4, a therapy to treat cancer, e.g., prostate cancer, is effected.

Those skilled in the art are familiar with various ways of deriving and using index values. For example, the index value may represent the copy number or concentration of a particular cell-free DNA listed as "UP" in Table 1 or Table 4 in a blood sample from a patient of interest in a healthy state, in which case a copy number or concentration in a sample from the patient at a different time or state significantly higher (e.g., 1.01-fold, 1.05-fold, 1.10-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 10-fold, 20-fold, 30-fold, 40-fold, 50-fold, 100-fold or more higher) than this index value would indicate, e.g., prostate cancer or increased likelihood of cancer recurrence. In some embodiments, the level of the CNA is "increased" if it is at least 1, 2, 3, 4, 5, 10, 15, 20 or more standard deviations greater than the index value in normal subjects. In some embodiments, an index value may represent the copy number or concentration of a particular cell-free DNA listed as "DOWN" in Table 1 or Table 4 in a blood sample from a patient of interest in a healthy state, in which case a copy number or concentration in a sample from the patient at a different time or state significantly lower (e.g., 1.01-fold, 1.05-fold, 1.10-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 10-fold, 20-fold, 30-fold, 40-fold, 50-fold, 100-fold or more lower) than this index value would indicate, e.g., prostate cancer or increased likelihood of prostate cancer recurrence. In some embodiments the level of the CNA is "decreased" if it is at least 1, 2, 3, 4, 5, 10, 15, 20 or more standard deviations lower than the index value in normal subjects Alternatively, the index value may represent the average concentration or copy number of a particular circulating cell-free DNA for a set of individuals from a diverse cancer population or a subset of the population. For example, one may determine the average copy number or concentration of a circulating cell-free DNA in a random sampling of patients with prostate cancer. Thus, patients having a copy number or concentration (test value) comparable to or higher than, this value identified as having an increased likelihood of having prostate cancer or prostate cancer recurrence than those having a test value lower than this value.

A useful index value may represent the copy number or concentration of a particular circulating cell-free DNA or of a combination (weighted or straight addition) of two or more circulating cell-free DNAs corresponding to the same chromosomal region or different chromosomal regions. When two or more biomarkers or circulating cell-free DNA molecules are used in the diagnosis/monitoring method, the level of each biomarker or circulating cell-free DNA can be weighted and combined. Thus, a test value may be provided by (a) weighting the determined level of each circulating cell-free DNA molecule with a predefined coefficient, and (b) combining the weighted level to provide a test value. The combining step can be either by straight addition or averaging (i.e., weighted equally) or by a different predefined coefficient.

The information obtained from the biomarker analysis may be stored in a computer readable form. Such a computer system typically comprises major subsystems such as a central processor, a system memory (typically RAM), an input/output (I/O) controller, an external device such as a display screen via a display adapter, serial ports, a keyboard, a fixed disk drive via a storage interface and a floppy disk drive operative to receive a floppy disc, and a CD-ROM (or DVD-ROM) device operative to receive a CD-ROM. Many other devices can be connected, such as a network interface connected via a serial port.

The computer system may also be linked to a network, comprising a plurality of computing devices linked via a data link, such as an Ethernet cable (coax or 10BaseT), telephone line, ISDN line, wireless network, optical fiber, or other suitable signal transmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

The computer system can comprise code for interpreting the results of a study evaluating the presence of one or more of the biomarkers. Thus in an exemplary embodiment, the biomarker analysis results are provided to a computer where a central processor executes a computer program for determining the likelihood of a patient that has prostate cancer.

The invention also provides the use of a computer system, such as that described above, which comprises: (1) a computer; (2) a stored bit pattern encoding the biomarker testing results obtained by the methods of the invention, which may be stored in the computer; (3) and, optionally, (4) a program for determining the likelihood of a patient having prostate cancer.

The invention further provides methods of generating a report based on the detection of one or more biomarkers set forth in Table 1 or Table 4.

Thus, the present invention provides systems related to the above methods of the invention. In one embodiment the invention provides a system for analyzing circulating cell-free DNA, comprising: (1) a sample analyzer for executing the method of analyzing circulating cell-free DNA in a patient's blood, serum or plasma as described in the various embodiments above (incorporated herein by reference); (2) a computer system for automatically receiving and analyzing data obtained in step (1) to provide a test value representing the status (presence or absence or amount, i.e., concentration or copy number) of one or more circulating cell-free DNA molecules having a nucleotide sequence of at least 25 nucleotides falling within a chromosomal region set forth in Table 1 or Table 4, and optionally for comparing the test value to one or more reference values each associated with a predetermined status of prostate cancer. In some embodiments, the system further comprises a display module displaying the comparison between the test value and the one or more reference values, or displaying a result of the comparing step.

Thus, as will be apparent to skilled artisans, the sample analyzer may be, e.g., a sequencing machine (e.g., Illumina HiSeg™, Ion Torrent PGM, ABI SOLiD™ sequencer, PacBio RS, Helicos Heliscope™, etc.), a PCR machine (e.g., ABI 7900, Fluidigm BioMark™, etc.), a microarray instrument, etc.

In one embodiment, the sample analyzer is a sequencing instrument, e.g., a next-generation sequencing instrument such as Roche's GS systems, Illumina's HiSeq and MiSeq, and Applied Biosystems' SOLiD systems. Circulating cell-free DNA molecules are isolated from a patient's blood or serum or plasma, and the sequences of all of the circulating cell-free DNA molecules are obtained using the sample analyzer. The sequencing instrument is used in sequencing the circulating cell-free DNA molecules, and obtaining the sequences of these molecules. A computer system is then employed for automatically analyzing the sequences to determine the level of a circulating cell-free DNA molecule having a nucleotide sequence of at least 25 nucleotides falling within a chromosomal region set forth in Table 1 or Table 4 in the sample. For example, the computer system may compare the sequence of each circulating cell-free DNA molecule in the sample to the sequence, available in the human sequence database, of the chromosomal region to determine if there is a match, i.e., if the sequence of a circulating cell-free DNA molecule falls within a chromosomal region set forth in Table 1 or Table 4. The copy number of a particular circulating cell-free DNA molecule is also automatically determined by the computer system. Optionally the computer system automatically correlates the sequence analysis result with a diagnosis regarding prostate cancer. For example, if one, and preferably two or more, circulating cell-free DNA molecules are identified to be derived from chromosomal regions designated as "UP" in Table 1 or Table 4 and present at an increased level, then the computer system automatically correlates this analysis result with a diagnosis of prostate cancer. If one, and preferably two or more, circulating cell-free DNA molecules are identified to be derived from chromosomal regions designated as "DOWN" in Table 1 or Table 4 and present at a decreased level, then the computer system automatically correlates this analysis result with a diagnosis of prostate cancer. Optionally, the computer system further comprises a display module displaying the results of sequence analysis and/or the result of the correlating step. The display module may be for example, a display screen, such as a computer monitor, TV monitor, or the touch screen, a printer, and audio speakers.

The computer-based analysis function can be implemented in any suitable language and/or browsers. For example, it may be implemented with C language and preferably using object-oriented high-level programming languages such as Visual Basic, SmallTalk, C++, and the like. The application can be written to suit environments such as the Microsoft Windows™ environment including Windows™ 98, Windows™ 2000, Windows™ NT, and the like. In addition, the application can also be written for the MacIntosh™, SUN™, UNIX or LINUX environment. In addition, the functional steps can also be implemented using a universal or platform-independent programming language. Examples of such multi-platform programming languages include, but are not limited to, hypertext markup language (HTML), JAVA™, JavaScript™, Flash programming language, common gateway interface/structured query language (CGI/SQL), practical extraction report language (PERL), AppleScript™ and other system script languages, programming language/structured query language (PL/SQL), and the like. Java™- or JavaScript™-enabled browsers such as HotJava™, Microsoft™ Explorer™, or Netscape™ can be used. When active content web pages are used, they may include Java™ applets or ActiveX™ controls or other active content technologies.

The analysis function can also be embodied in computer program products and used in the systems described above or other computer- or internet-based systems. Accordingly, another aspect of the present invention relates to a computer program product comprising a computer-usable medium having computer-readable program codes or instructions embodied thereon for enabling a processor to carry out the analysis and correlating functions as described above. These computer program instructions may be loaded onto a computer or other programmable apparatus to produce a machine, such that the instructions which execute on the computer or other programmable apparatus create means for implementing the functions or steps described above. These computer program instructions may also be stored in a computer-readable memory or medium that can direct a computer or other programmable apparatus to function in a particular manner, such that the instructions stored in the computer-readable memory or medium produce an article of manufacture including instruction means which implement the analysis. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

In some embodiments, once it has been determined Assessment of Total CNI in Cell-Free Circulating DNA In another aspect, the invention provides a method of evaluating the total severity of chromosomal rearrangement in a patient with cancer, such as prostate cancer, irrespective of the site of the chromosomal region. Accordingly, the degree or amount of chromosomal rearrangements in the cancer cells from the patient can be transformed into a biomarker score.

Cell-free circulating DNA can be sequenced using methods described herein. The number of sequences that map to unique regions of the genome can be determined. Methods of quantifying the levels of in a patient compared to normal controls are known in the art. In this embodiment, using circulating DNA as measure, such a score can be calculated in different ways e.g., by using restricted counts or sums, by using other reference material (e.g. genomic DNA) or other distribution models than the Gaussian or using different cut-offs for positivity or combinations of such. Such scoring will be typically dependent on the technology used as well as on the number or sequence reads that are generated for any sample.

For example, in some embodiments, the CNIscore from a patient may be compared to an index value CNIscore for normal individuals. Thus, for example, a CNIscore indicative of a cancer, e.g., prostate cancer, may be at least 1, 2, 3, 4, 5, 10, 15, 20 or more standard deviations from the index value in normal subjects. In some embodiments, a patient that is determined to have a CNIscore indicative of cancer, e.g., prostate cancer receives a therapy to treat the cancer, e.g., radiation, chemotherapy, hormone therapy, etc.

The following examples are provided by way of illustration only and not by way of limitation. Those of skill in the art will readily recognize a variety of non-critical parameters that could be changed or modified to yield essentially similar results.

EXAMPLES

Example 1

Identification of Prostate Cancer (PrCa) Associate CNA

Study Samples

The study evaluated 204 serum samples obtained from patients with prostate cancer (e.g., having a histopathology report of invasive prostate carcinoma), 20 samples from other medical conditions and 207 serum samples from healthy (e.g., defined as asymptomatic or have a negative biopsy) controls. Sample sets from multiple centers were used in the trial, where for each given set of cases, their corresponding matching controls originated from the same center. Patient serum samples were obtained from different sites: Ryazan Central Oblast Hospital, Russia (n=100), Dr. Narod in Toronto (n=200), and commercial vendors (e.g., Proteogenex), to achieve a total number of at least 200 cases and 200 matched controls. Of the 200 cases, 89 patients had a Gleason score<7 and 76 cases were from patients diagnosed at ≤65 years of age. Blood was drawn preoperatively from treatment-naïve patients under local IRB approval and processed as described previously (Beck et al., *Clin. Chem.* 55:730-738, 2009).

Patient samples were run in batches that are built to include cases and controls in each batch to ensure avoidance of batch effects. After initial analyses samples were analyzed in silico using randomly assigned training validation sets in an appropriate number of rounds for cluster analysis.

Construction of Sequencing Libraries

After extraction of DNA from serum or plasma, using a standard silica-based method, a whole genome amplification was performed in duplicate. The products of the two reactions were pooled and used for further analysis. In particular, DNA was extracted from ≥200 μL fo each sample and used for two independent amplifications using the Genomeplex kit for single cell (Sigma). The P2 adapter used for sequencing and a 10 bp sample-specific nucleotide sequence (also referred to as molecular barcode) are added by PCR using fusion-primers. Two consecutive PCRs with different fusion-primers were performed; the total number of cycles was four. Following the PCRs, the tagged DNA of up to 50 samples was pooled and all further preparations were performed on this pooled DNA material. Further library preparation steps were as follows:

i) Restriction of DNA with endonuclease NlaIII;
ii) Removal of the 3' overhangs created by NlaIII using the Large Klenow Fragment;
iii) Ligation of P1 (second sequencing adapter that in some instances contains a 10-bp molecular barcode sequence) to the blunted ends;
iv) Amplification of the library by a maximum of 10 cycles of PCR using primers complementary to the P1/P2 adapters of the fragments; and
v) Size-selection using the iBase electrophoresis system and 2% E-Gel size selection agarose gels (Invitrogen) to obtain fragments in the range of 150-250 bp.

Sequencing

Sequencing of the libraries was performed on a SOLiD4+ Instrument (Applied Biosystems) equipped with an EZBead-System (Applied Biosystems) for conducting the emulsion PCRs. All necessary reagents were purchased from Applied Biosystems. Emulsion PCRs and sequencing was performed as recommended by the manufacturer. For some libraries the first ten bases of each read constitute the molecular barcode, therefore, the net read length used for mapping was 40 bp. For other libraries, the barcode sequences is located between an internal adapter and the P2 adapter. The barcode sequences were obtained in separate sequencing cycles. Therefore the full length of the P1 read (50 bp) was used for mapping against the human genome.

Data Analysis

The sequence reads were assigned to the different samples according to the sequence of the molecular barcode. A total of ten slides were used for the entire study.

The sequences were mapped to the human genome (Build 36.1/Hg18) and results are stored in binary alignment map files (BAM). Alignment of raw SOLiD reads were performed using the software BioScope™ ver. 1.2 (Applied Biosystems). These were used as input data to calculate "hit counts in" bins of 100 kbp with a 50 kbp sliding window using the software suite BedTools ver. 2.14.2 (University of Virginia, Charlottesville, Va.). Table 2 shows an example of the analysis output of one sample and chromosome. From these files the chromosome, bin position and read count were used as input for subsequent analyses.

Once the reads counts per bin were determined for each sample (secondary data), the secondary data were used for an in silico training-validation study. From each, the group of cases and the control group, 50% were randomly assigned to the training set and evaluated (e.g. in an unsupervised cluster search). The resulting clusters were then applied to the remaining 50% of samples (validation set). This procedure was repeated 1227 times per sample set or sample subset.

Regions of genomic deviation in cancer were selected from the randomized training/validation, by means of their segregating power and used in a final model to be applied on the whole set, or subsets to be evaluated individually (e.g. regional subsets). Standard ROC analyses along with some categorical analyses were used to evaluate signature performance in the trial overall and among sub-groups of interest.

All data were first normalized to their total counts, matching the HG 18 in a uniquely manner. To account for slide-to-slide variations, the counts per bin were normalized to the ratio per bin and slide using only samples assigned to the control group using the following equations:

$$\text{run/slide}(i): x_{n,bin} = \frac{count_{n,bin}}{\sum_{bin=1}^{bin=56684} count_{n,bin}} \quad \text{Equation 1}$$

where:

$count_{n,\,bin}$ is the number of reads per bin of an individual (n) as given in the BED-files. The formula above shows the Global normalization; for Local normalization the divisor is per interrogated chromosome.

Followed by:

$$\dot{Y}_{n,i,bin} = \frac{x_{n,i,bin} \times \bar{x}_{i,bin}}{\bar{x}_{all,bin}} \quad \text{Equation 2}$$

where:

$x_{n,\,i,\,bin}$ is for each bin the normalized read count of the individual (n) on slide (i)

$\bar{x}_{i,\,bin}$ is the average per bin over normal individuals on a slide (i)

$\bar{x}_{all,\,bin}$ is the average per bin over normal individuals on all slides $\bar{X}_{i,bin}$ and $\bar{X}_{all,bin}$ are stored for subsequent calculations.

The $\dot{Y}$ values are calculated on the fly for the final definition of diagnostic genomic clusters using an unsupervised cluster search as follows:

The first step of the unsupervised cluster search (UCS) was:

1) Normalization of the reads (per sample)
   a. Global->total reads as basis
   b. Local->read per chromosome as basis For 1228 rounds, the data were randomized into training (50%) and validation set (50%). The training sets were used to:

1) Optimize clusters that segregated disease from control group by
   a. Combining consecutive clusters (add $\dot{Y}$ of next bin)
   b. Stopping at maximum of either:
      i. #disease<k—smallest control
      ii. #disease>k—largest control
2) Record when optimum were found and # disease>19, otherwise go to 3):
   a. Normalization (Global/Local)
   b. Chromosome c. Optimized region (start-stop)
d. #disease samples positive in training set
e. #disease samples positive in validation set using:
  i. delimiter from training set
  ii. delimiter from validation set (according to 1b)
f. C-Statistics
g. values for each sample in (segregated disease/control)
  i. training set
  ii. validation set
3) Perform analysis on next window The next randomization was performed and the data recorded into a new table. All regions identified from the UCS above were combined and ranked according to their number of occurrences in the 1228 rounds. Figure illustrates a flowchart of the UCS. In this study k was set to 4.

The result for each sample was then retrieved for the 100 highest ranking regions (Table 3) and further processed for controls and prostate cancer.

A Stepwise procedure comprising stepwise out and stepwise in was used to select the final regions. In Stepwise out, the data were then cleaned for cross-correlated regions (all regions that did not have more than 14 samples with deviating results were censored). Subsequently, regions that do not have additional information content over other regions were eliminated in a step-wise out approach, where the first 10 regions (highest ranks) were excluded herein. In Stepwise in, a classical stepwise in procedure was used up to the point where the information content of the combined data does reach its limit herein. The results of both procedural directions are given in Table 3. For the final region selection, regions that hold in both stepwise procedures were considered. This resulted in 27 regions to be used as final candidates, which was followed by introducing a weighting factor for final optimization on those 27 regions, which hold in the preceding step. Table 4 shows the final selected regions. Table 5 shows the cross-correlation between selected regions.

For each region the delimiter was set to the value corresponding to k-smallest $\dot{Y}_{region}$ value of controls for regions denoted "Down" and to the k-largest $\dot{Y}_{region}$ value of controls for regions denoted "Up" respectively. Any $\dot{Y}_{region}$ value greater than a delimiter for region denoted "UP" or lower than a delimiter for regions denoted "Down" was assigned a Score value of 1. Else the score was set to 0. Using k=6, for each control and patient sample the CHX-Index was then calculated as:

$$CHXindex = \sum_{region=1}^{27} Score \times Weight \qquad \text{Equation 3}$$

The ROC data are calculated from the CHX-Index. ROC curves with 95% confidence intervals were then calculated from the data using the statistical software "Analyse-it for Excel vers. 2.26 (Analyse-it Software, Ltd.).
Results The AURoC was 92.7% (CI: 0.902-0.951) when comparing 204 PrCa samples vs 207 Controls (see, Table 6). The AURoC was above 85% for the following queries tested: PrCa vs Controls, PrCA vs Controls which included ten benign prostate hyperplasia and ten prostatitis samples, Gleason scores below to, or above and equal 7 and age≤65.

Two different library construction and sequencing approaches were tested in the study. For a set of slides, the barcode sequence was positioned within the first 10 bp of the 50 bp sequencing read, leaving 40 bp usable for mapping. And for another set of slides, separate barcode sequencing was performed leaving 50 bp usable for mapping. AURoC values were obtained for each subgroup. The AURoC was 0.91 for 40 bp reads and 0.95 for 50 bp. Although not statistically significantly (p=0.06) different, the trend leads to the conclusion, that for future studies 50 bp or higher would be preferable.

The other medical conditions (OMC) samples consisted of ten benign prostate hyperplasia and ten prostatitis samples. These were not included in the UCS, but added as additional controls for confirmation. The ROC AUC, when adding these samples were not deteriorating compared to the original set, which serves as additional proof for the usage of the selected regions.

The results of the CHX analysis were compared to those samples know to have a PSA result. Figure shows the scatter plot from a non-parametric Spearman Rank Correlation analysis. The correlation of the CHX and PSA tests had a R(S)-value of 0.501 (0.398 to 0.591), t-value:8.82corresponding to a p-value of $2.8 \times 10^{-16}$. The PSA levels of 22 control individuals were >5.0 µg/l; these individuals have been followed for at least 2 years, without any sign of prostate cancer and were therefore assigned to the control group (N.B. the PSA determination was based on the older standard; values for the reference WHO 96/670 are about 80%, the value of 5.0 above corresponds to 4.0 according to the reference standard).

Example 2

Evaluation of Copy Number Index for Circulating Cell-Free DNA in Prostate Cancer Patients Copy number instabilities/variations are a known characteristic of malignancies. Therefore, cell-free DNA samples from individual patients were analyzed to determine whether tumor-derived copy number instabilities are quantitatively reflected in the circulating DNA of individual patients. In this example, it is not chromosomal regions that are predominantly seen in this tumor patient group that were used, but the total severity of chromosomal rearrangements in an individual patient with cancer, irrespective of the chromosomal location was transformed into a biomarker (CNIscore).

Figure 3:
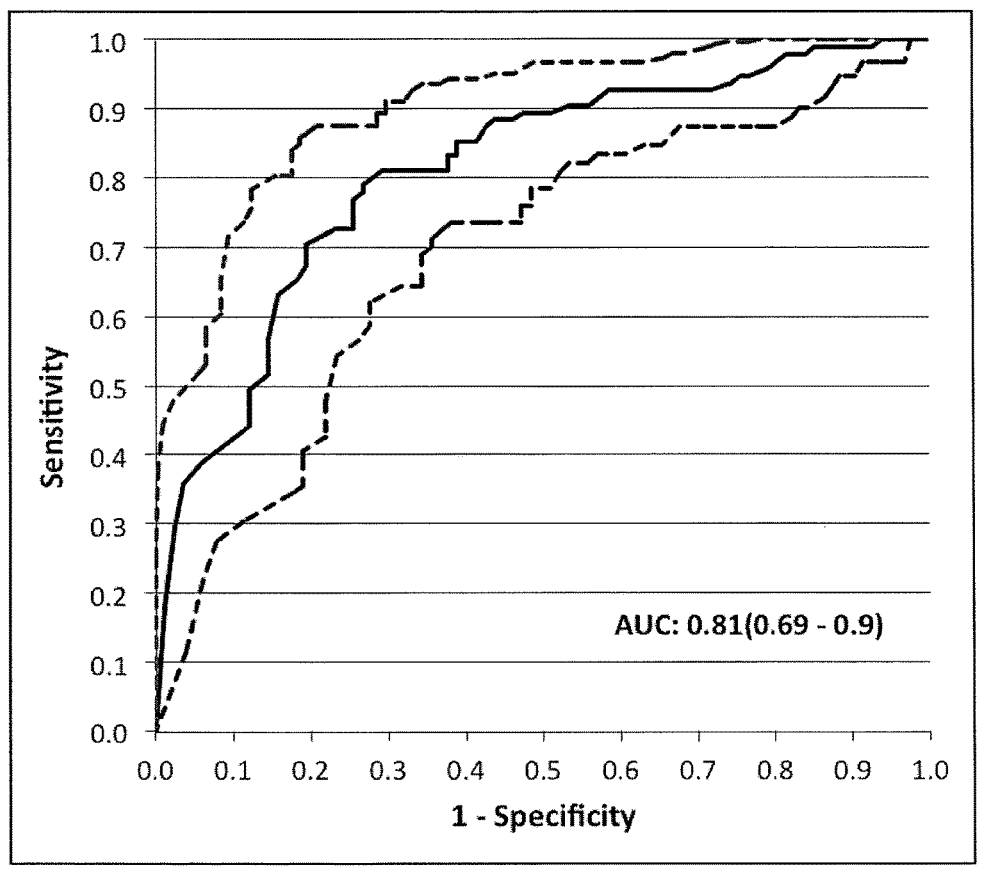
FIG. 3 shows a ROC curve using the Copy Number Instability (CNI) score in circulating nucleic acids (CAN); Z-scores of >2 were summed in each individual to generate the score.
Figure 4A:
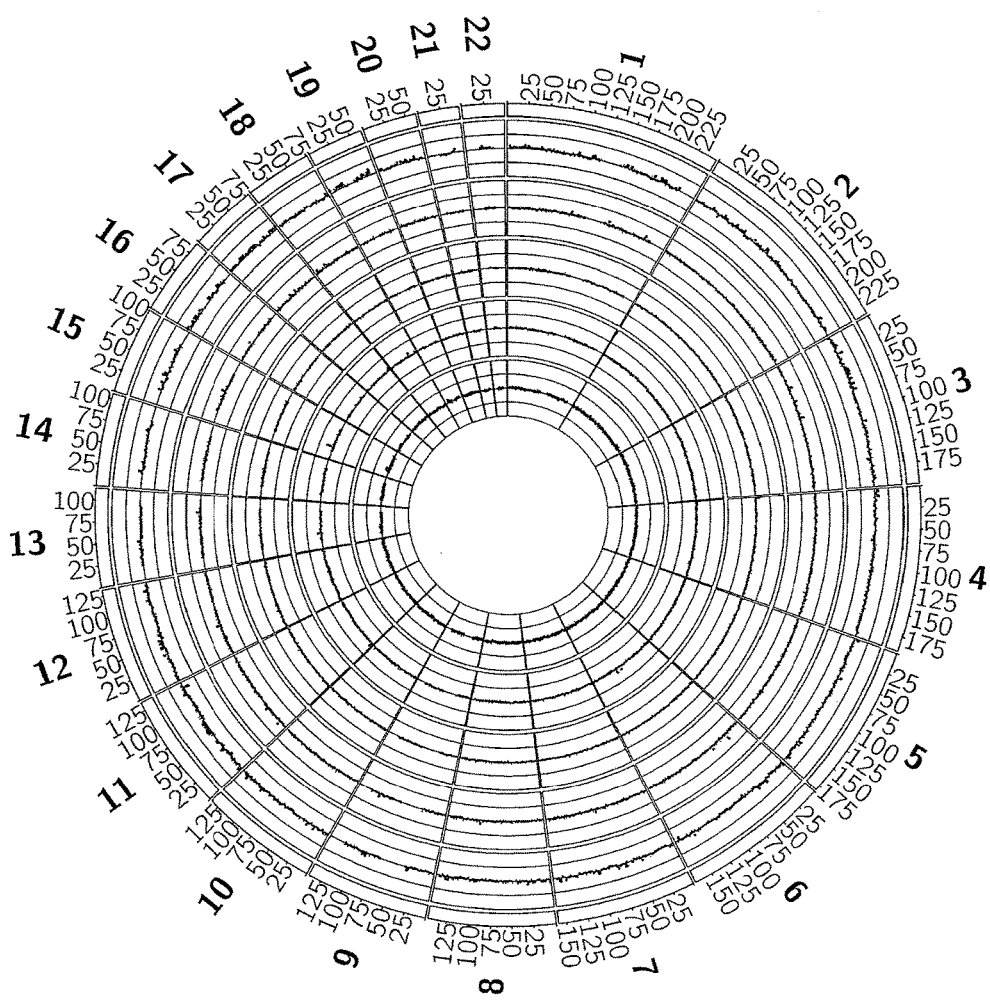
FIGS. 4(a) and (b) provide an example showing the CNA copy number variations (Z-values) in five normal individuals (a) compared to five prostate cancer patients (b). The outer tracks represent the human chromosomes, chromosomal positions in Mbp are indicated. Each inner circular track represents data for one individual. Significant data points with values>2 or <-2 are highlighted by a larger glyph size. Each data track's y-axis spans from −20 to 20, the two sub-scales indicate values of −10 and 10.
Figure 4B:
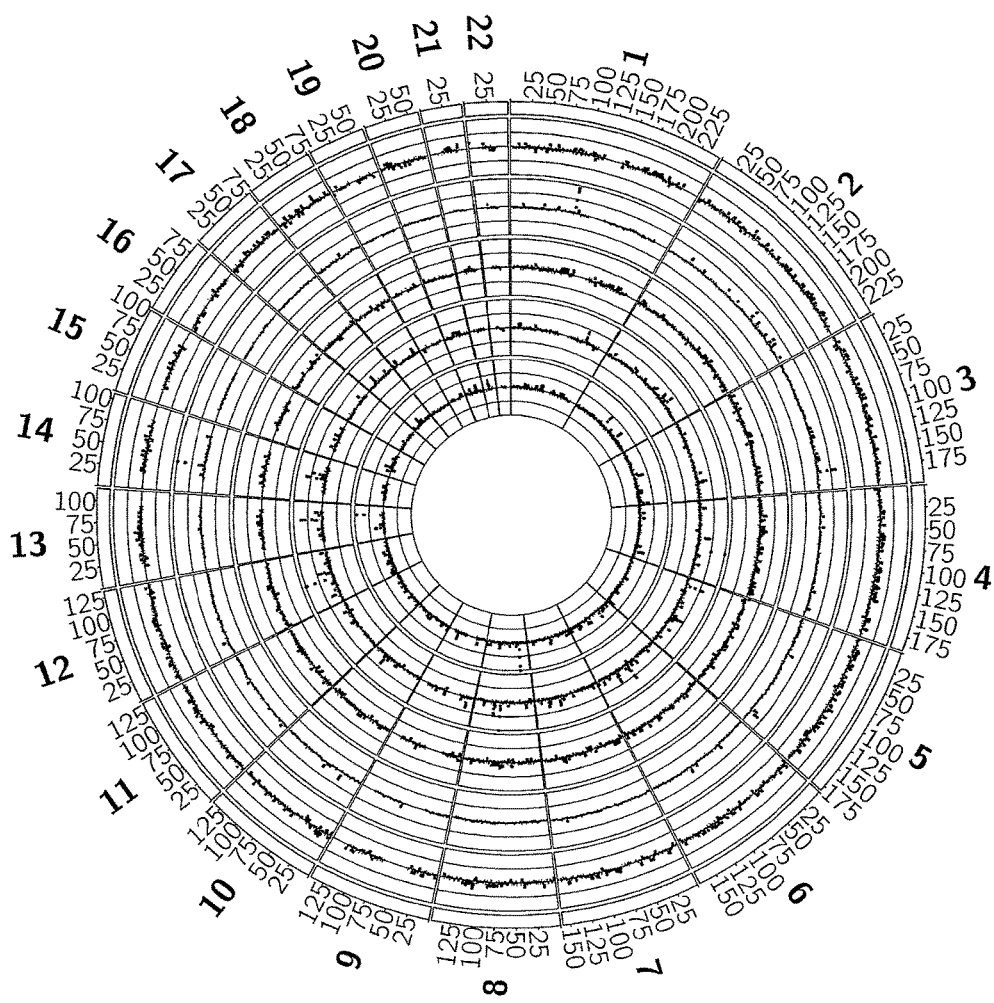

For this exampless, LOESS normalized sequence read counts (cf Equation 2) from a subset of samples that consisted of fresh drawn samples with total mappable reads of >1.3 million reads were used for defining a CNI severity score. The samples were stratified into those from normal male individuals (N=95) and those from prostate cancer patients (N=82). For each 100 kilo basepair bin, the normalized read counts were transferred into Z-values $$\left( Z = \frac{X_i - \overline{X}_{norm}}{SD_{norm}} \right).$$

followed by a Parzen-Rosenblatt smoothing (Parzen E (1962) *Annals of Mathematical Statistics* 33: 1065-1076; Rosenblatt M (1956) *Annals of Mathematical Statistics* 27: 832-837). For each sample, it was calculated how many bins were found to exhibit a Z-value>1, >2, >3, >4, >5, and so forth. The number of such genomic 100 kbp windows (with copy numbers deviating from the normal group at a given Z-value level), were then counted as a summative score (CNIscore). In addition, the absolute Z-Scores above (and below) a certain border can be summed up to generate a CNIscore. When using the border of Z>2, the resulting ROC curve from the sum CNIscore is shown in FIG. 3. The AUC to separate the prostate cancer from normals was 0.81 for the global normalization and 0.80 for local normalization (not shown). FIG. 4 provides an exemplification of such copy number deviations. FIG. 4a provides a CIROCS plot (Krzywinski, et al. *Genome Res* (2009) 19:1639-1645) of five normal individuals, showing the CNA Z-values. In comparing the CIRCOS plot from the normal individual to a CIRCOS plot (FIG. 4b) of five representative prostate cancer patients, it can clearly be seen that prostate cancer samples exhibited a high accumulation of CNIs in the circulating DNA scattering throughout the genome (only data from global normalization are shown).

All patents, patent applications, and other published reference materials cited in this specification are hereby incorporated herein by reference in their entirety for their disclosures of the subject matter in whose connection they are cited herein.

TABLE 1

Chromosomal Regions Selected from 1228 runs of randomly selected 50% training sets

| # | Chromosome | Region | Start | Stop | Up/Down | Normalization |
|---|---|---|---|---|---|---|
| 1 | Hs8 | 43050001-43250000 | 43050001 | 43250000 | UP | Global |
| 2 | Hs15 | 61450001-61750000 | 61450001 | 61750000 | UP | Local |
| 3 | Hs1 | 212200001-212400000 | 212200001 | 212400000 | DOWN | Global |
| 4 | Hs8 | 43150001-43350000 | 43150001 | 43350000 | UP | Local |
| 5 | Hs13 | 21200001-21800000 | 21200001 | 21800000 | DOWN | Local |
| 6 | Hs17 | 58300001-58500000 | 58300001 | 58500000 | UP | Local |
| 7 | Hs15 | 61500001-61900000 | 61500001 | 61900000 | UP | Global |
| 8 | Hs1 | 148450001-148650000 | 148450001 | 148650000 | UP | Local |
| 9 | Hs17 | 58250001-58550000 | 58250001 | 58550000 | UP | Local |
| 10 | Hs5 | 11200001-11600000 | 11200001 | 11600000 | DOWN | Local |
| 11 | Hs8 | 43150001-43250000 | 43150001 | 43250000 | UP | Global |
| 12 | Hs10 | 17900001-18200000 | 17900001 | 18200000 | UP | Local |
| 13 | Hs15 | 61500001-61800000 | 61500001 | 61800000 | UP | Local |
| 14 | Hs9 | 88650001-88750000 | 88650001 | 88750000 | UP | Local |
| 15 | Hs15 | 61350001-61750000 | 61350001 | 61750000 | UP | Local |
| 16 | Hs9 | 88650001-88750000 | 88650001 | 88750000 | UP | Global |
| 17 | Hs1 | 88950001-89450000 | 88950001 | 89450000 | UP | Local |
| 18 | Hs2 | 132950001-133150000 | 132950001 | 133150000 | DOWN | Local |
| 19 | Hs4 | 41850001-42050000 | 41850001 | 42050000 | DOWN | Local |
| 20 | Hs10 | 89050001-89250000 | 89050001 | 89250000 | UP | Local |
| 21 | Hs8 | 43100001-43400000 | 43100001 | 43400000 | UP | Local |
| 22 | Hs2 | 230150001-230450000 | 230150001 | 230450000 | UP | Global |
| 23 | Hs4 | 186750001-187250000 | 186750001 | 187250000 | DOWN | Local |
| 24 | Hs10 | 27600001-27900000 | 27600001 | 27900000 | UP | Local |
| 25 | Hs10 | 109750001-110050000 | 109750001 | 110050000 | UP | Global |
| 26 | Hs8 | 43100001-43400000 | 43100001 | 43400000 | UP | Global |
| 27 | Hs13 | 21250001-21750000 | 21250001 | 21750000 | DOWN | Local |
| 28 | Hs3 | 55450001-55650000 | 55450001 | 55650000 | DOWN | Local |
| 29 | Hs16 | 67750001-67950000 | 67750001 | 67950000 | UP | Local |
| 30 | Hs3 | 55400001-55700000 | 55400001 | 55700000 | DOWN | Local |
| 31 | Hs2 | 132950001-133250000 | 132950001 | 133250000 | DOWN | Global |
| 32 | Hs20 | 32450001-32550000 | 32450001 | 32550000 | UP | Local |
| 33 | Hs13 | 21300001-21800000 | 21300001 | 21800000 | DOWN | Local |
| 34 | Hs22 | 28650001-28850000 | 28650001 | 28850000 | UP | Local |
| 35 | Hs16 | 57450001-57750000 | 57450001 | 57750000 | UP | Local |
| 36 | Hs10 | 27650001-27850000 | 27650001 | 27850000 | UP | Local |
| 37 | Hs2 | 64850001-64950000 | 64850001 | 64950000 | UP | Local |
| 38 | Hs22 | 28600001-28900000 | 28600001 | 28900000 | UP | Local |
| 39 | Hs10 | 109750001-110050000 | 109750001 | 110050000 | UP | Local |
| 40 | Hs1 | 148550001-148750000 | 148550001 | 148750000 | UP | Local |
| 41 | Hs4 | 186600001-187100000 | 186600001 | 187100000 | DOWN | Local |
| 42 | Hs22 | 30100001-30300000 | 30100001 | 30300000 | UP | Local |
| 43 | Hs1 | 88800001-89500000 | 88800001 | 89500000 | UP | Local |
| 44 | Hs20 | 16000001-16200000 | 16000001 | 16200000 | DOWN | Global |
| 45 | Hs20 | 40000001-40200000 | 40000001 | 40200000 | DOWN | Global |
| 46 | Hs6 | 58450001-58550000 | 58450001 | 58550000 | UP | Global |
| 47 | Hs11 | 10100001-10300000 | 10100001 | 10300000 | UP | Local |
| 48 | Hs20 | 57850001-58250000 | 57850001 | 58250000 | UP | Local |
| 49 | Hs17 | 54550001-54750000 | 54550001 | 54750000 | UP | Local |
| 50 | Hs10 | 32950001-33150000 | 32950001 | 33150000 | UP | Local |
| 51 | Hs16 | 45650001-45950000 | 45650001 | 45950000 | UP | Global |
| 52 | Hs20 | 42300001-42700000 | 42300001 | 42700000 | UP | Local |
| 53 | Hs10 | 17900001-18200000 | 17900001 | 18200000 | UP | Global |
| 54 | Hs13 | 18350001-18650000 | 18350001 | 18650000 | DOWN | Local |
| 55 | Hs2 | 47750001-47850000 | 47750001 | 47850000 | DOWN | Global |
| 56 | Hs2 | 64850001-64950000 | 64850001 | 64950000 | UP | Global |
| 57 | Hs1 | 197450001-197750000 | 197450001 | 197750000 | UP | Global |
| 58 | Hs2 | 133000001-133400000 | 133000001 | 133400000 | DOWN | Global |
| 59 | Hs8 | 42950001-43350000 | 42950001 | 43350000 | UP | Local |
| 60 | Hs2 | 230150001-230450000 | 230150001 | 230450000 | UP | Local |
| 61 | Hs8 | 120750001-120950000 | 120750001 | 120950000 | UP | Local |

TABLE 1-continued

Chromosomal Regions Selected from 1228 runs of randomly selected 50% training sets

| # | Chromosome | Region | Start | Stop | Up/Down | Normalization |
|---|---|---|---|---|---|---|
| 62 | Hs13 | 69050001-69250000 | 69050001 | 69250000 | UP | Global |
| 63 | Hs17 | 58350001-58550000 | 58350001 | 58550000 | UP | Local |
| 64 | Hs2 | 47750001-47850000 | 47750001 | 47850000 | DOWN | Local |
| 65 | Hs12 | 44300001-44400000 | 44300001 | 44400000 | UP | Global |
| 66 | Hs12 | 109500001-109600000 | 109500001 | 109600000 | UP | Local |
| 67 | Hs6 | 58450001-58550000 | 58450001 | 58550000 | UP | Local |
| 68 | Hs1 | 219250001-219650000 | 219250001 | 219650000 | UP | Local |
| 69 | Hs12 | 128050001-128650000 | 128050001 | 128650000 | DOWN | Local |
| 70 | Hs20 | 42500001-42700000 | 42500001 | 42700000 | UP | Local |
| 71 | Hs2 | 133050001-133350000 | 133050001 | 133350000 | DOWN | Global |
| 72 | Hs7 | 86350001-86450000 | 86350001 | 86450000 | UP | Global |
| 73 | Hs4 | 186800001-187200000 | 186800001 | 187200000 | DOWN | Local |
| 74 | Hs20 | 39950001-40150000 | 39950001 | 40150000 | DOWN | Global |
| 75 | Hs1 | 88850001-89450000 | 88850001 | 89450000 | UP | Local |
| 76 | Hs12 | 127950001-128650000 | 127950001 | 128650000 | DOWN | Local |
| 77 | Hs2 | 133000001-133400000 | 133000001 | 133400000 | DOWN | Local |
| 78 | Hs7 | 86350001-86450000 | 86350001 | 86450000 | UP | Local |
| 79 | Hs2 | 230250001-230450000 | 230250001 | 230450000 | UP | Local |
| 80 | Hs12 | 127950001-128650000 | 127950001 | 128650000 | DOWN | Global |
| 81 | Hs12 | 44300001-44400000 | 44300001 | 44400000 | UP | Local |
| 82 | Hs8 | 42950001-43350000 | 42950001 | 43350000 | UP | Global |
| 83 | Hs2 | 186650001-186750000 | 186650001 | 186750000 | UP | Global |
| 84 | Hs17 | 61300001-61800000 | 61300001 | 61800000 | DOWN | Global |
| 85 | Hs2 | 133050001-133350000 | 133050001 | 133350000 | DOWN | Local |
| 86 | Hs12 | 109500001-109600000 | 109500001 | 109600000 | UP | Global |
| 87 | Hs9 | 114800001-114900000 | 114800001 | 114900000 | UP | Local |
| 88 | Hs6 | 58350001-58550000 | 58350001 | 58550000 | UP | Global |
| 89 | Hs2 | 234200001-234700000 | 234200001 | 234700000 | DOWN | Local |
| 90 | Hs8 | 120750001-121050000 | 120750001 | 121050000 | UP | Global |
| 91 | Hs6 | 58400001-58600000 | 58400001 | 58600000 | UP | Global |
| 92 | Hs8 | 67600001-67700000 | 67600001 | 67700000 | UP | Global |
| 93 | Hs2 | 235800001-236100000 | 235800001 | 236100000 | DOWN | Local |
| 94 | Hs7 | 69900001-70100000 | 69900001 | 70100000 | DOWN | Local |
| 95 | Hs12 | 128050001-128650000 | 128050001 | 128650000 | DOWN | Global |
| 96 | Hs16 | 75950001-76350000 | 75950001 | 76350000 | DOWN | Global |
| 97 | Hs2 | 98700001-98900000 | 98700001 | 98900000 | UP | Global |
| 98 | Hs12 | 95400001-95600000 | 95400001 | 95600000 | UP | Local |
| 99 | Hs2 | 20200001-20500000 | 20200001 | 20500000 | DOWN | Local |
| 100 | Hs13 | 21100001-21800000 | 21100001 | 21800000 | DOWN | Local |

TABLE 2

Example of BED-Files (one file per sample and chromosome).

| Chromosome | bin-Start | bin-Stop | #reads | bases covered | bin size | Q-bp covered |
|---|---|---|---|---|---|---|
| chr22 | 15150001 | 15250000 | 1 | 49 | 99999 | 0.00049 |
| chr22 | 15200001 | 15300000 | 9 | 225 | 99999 | 0.00225 |
| chr22 | 15250001 | 15350000 | 21 | 548 | 99999 | 0.0054801 |
| chr22 | 15300001 | 15400000 | 16 | 511 | 99999 | 0.0051101 |
| chr22 | 15350001 | 15450000 | 8 | 329 | 99999 | 0.00329 |
| chr22 | 15400001 | 15500000 | 10 | 337 | 99999 | 0.00337 |
| chr22 | 15450001 | 15550000 | 32 | 561 | 99999 | 0.0056101 |
| chr22 | 15500001 | 15600000 | 38 | 752 | 99999 | 0.0075201 |
| chr22 | 15550001 | 15650000 | 40 | 1160 | 99999 | 0.0116001 |
| chr22 | 15600001 | 15700000 | 59 | 1499 | 99999 | 0.0149901 |
| chr22 | 15650001 | 15750000 | 38 | 1000 | 99999 | 0.0100001 |
| chr22 | 15700001 | 15800000 | 38 | 1046 | 99999 | 0.0104601 |
| chr22 | 15750001 | 15850000 | 52 | 1462 | 99999 | 0.0146201 |
| chr22 | 15800001 | 15900000 | 38 | 1119 | 99999 | 0.0111901 |
| chr22 | 15850001 | 15950000 | 54 | 1338 | 99999 | 0.0133801 |
| chr22 | 15900001 | 16000000 | 55 | 1417 | 99999 | 0.0141701 |
| chr22 | 15950001 | 16050000 | 42 | 1162 | 99999 | 0.0116201 |
| chr22 | 16000001 | 16100000 | 43 | 1250 | 99999 | 0.0125001 |
| chr22 | 16050001 | 16150000 | 46 | 1117 | 99999 | 0.0111701 |
| chr22 | 16100001 | 16200000 | 60 | 1319 | 99999 | 0.0131901 |
| chr22 | 16150001 | 16250000 | 66 | 1664 | 99999 | 0.0166402 |
| chr22 | 16200001 | 16300000 | 99 | 2245 | 99999 | 0.0224502 |

TABLE 3

Results of the stepwise selection procedure of the 100 highest ranking regions as in Table 1

| | Regions: 27 | FINAL (204|207) | AUC | | AUC |
|---|---|---|---|---|---|
| | | | 0.922385621 | | 0.926719238 |

| # | Stepwise Out | Stepwise IN | | | | Weight |
|---|---|---|---|---|---|---|
| 1 | 1.5 | 1.5 | Gchr8 | 43050001-43250000 | 1 | 1.5 |
| 2 | 1 | 0 | Lchr15 | 61450001-61750000 | 0 | 0 |
| 3 | 0.49 | 0.49 | Gchr1 | 212200001-212400000 | 1 | 0.49 |
| 4 | 0.49 | 0 | Lchr8 | 43150001-43350000 | 0 | 0 |
| 5 | 0.49 | 0 | Lchr13 | 21200001-21800000 | 0 | 0 |
| 6 | 0.49 | 1 | Lchr17 | 58300001-58500000 | 1 | 1.5 |
| 7 | 1 | 1 | Gchr15 | 61500001-61900000 | 1 | 1 |
| 8 | 0.49 | 1 | Lchr1 | 148450001-148650000 | 1 | 0.49 |
| 9 | 0.49 | 0 | Lchr17 | 58250001-58550000 | 0 | 0 |
| 10 | 0 | 0 | Lchr5 | 11200001-11600000 | 0 | 0 |
| 11 | 0 | 0 | Gchr8 | 43150001-43250000 | 0 | 0 |
| 12 | 1 | 1.5 | Lchr10 | 17900001-18200000 | 1 | 1.5 |
| 13 | 0 | 0 | Lchr15 | 61500001-61800000 | 0 | 0 |
| 14 | 1 | 1.5 | Lchr9 | 88650001-88750000 | 1 | 1.5 |
| 15 | 0 | 1 | Lchr15 | 61350001-61750000 | 0 | 0 |
| 16 | 0 | 1 | Gchr9 | 88650001-88750000 | 0 | 0 |
| 17 | 0 | 0 | Lchr1 | 88950001-89450000 | 0 | 0 |
| 18 | 0 | 0 | Lchr2 | 132950001-133150000 | 0 | 0 |
| 19 | 0 | 0 | Lchr4 | 41850001-42050000 | 0 | 0 |

TABLE 3-continued

Results of the stepwise selection procedure of the 100 highest ranking regions as in Table 1

| | | | | | | |
|---|---|---|---|---|---|---|
| 20 | 1 | 1 | Lchr10 | 89050001-89250000 | 1 | 1 |
| 21 | 0 | 0 | Lchr8 | 43100001-43400000 | 0 | 0 |
| 22 | 1 | 0 | Gchr2 | 230150001-230450000 | 0 | 0 |
| 23 | 0 | 0 | Lchr4 | 186750001-187250000 | 0 | 0 |
| 24 | 1 | 1 | Lchr10 | 27600001-27900000 | 1 | 1 |
| 25 | 0 | 0 | Gchr10 | 109750001-110050000 | 0 | 0 |
| 26 | 0 | 0 | Gchr8 | 43100001-43400000 | 0 | 0 |
| 27 | 1 | 1 | Lchr13 | 21250001-21750000 | 1 | 1 |
| 28 | 0 | 0 | Lchr3 | 55450001-55650000 | 0 | 0 |
| 29 | 1 | 1 | Lchr16 | 67750001-67950000 | 1 | 1 |
| 30 | 0.49 | 0 | Lchr3 | 55400001-55700000 | 0 | 0 |
| 31 | 0 | 0 | Gchr2 | 132950001-133250000 | 0 | 0 |
| 32 | 0 | 0 | Lchr20 | 32450001-32550000 | 0 | 0 |
| 33 | 1 | 1 | Lchr13 | 21300001-21800000 | 1 | 1 |
| 34 | 0 | 1 | Lchr22 | 28650001-28850000 | 0 | 0 |
| 35 | 0.49 | 0 | Lchr16 | 57450001-57750000 | 0 | 0 |
| 36 | 1 | 1 | Lchr10 | 27650001-27850000 | 1 | 1 |
| 37 | 0 | 0 | Lchr2 | 64850001-64950000 | 0 | 0 |
| 38 | 0 | 0 | Lchr22 | 28600001-28900000 | 0 | 0 |
| 39 | 0 | 0 | Lchr10 | 109750001-110050000 | 0 | 0 |
| 40 | 0 | 0 | Lchr1 | 148550001-148750000 | 0 | 0 |
| 41 | 1 | 1 | Lchr4 | 186600001-187100000 | 1 | 1 |
| 42 | 0 | 1 | Lchr22 | 30100001-30300000 | 0 | 0 |
| 43 | 0 | 1 | Lchr1 | 88800001-89500000 | 0 | 0 |
| 44 | 0 | 1 | Gchr20 | 16000001-16200000 | 0 | 0 |
| 45 | 0 | 0 | Gchr20 | 40000001-40200000 | 0 | 0 |
| 46 | 1 | 1 | Gchr6 | 58450001-58550000 | 1 | 1 |
| 47 | 1 | 0 | Lchr11 | 10100001-10300000 | 0 | 0 |
| 48 | 1 | 1 | Lchr20 | 57850001-58250000 | 1 | 1 |
| 49 | 0 | 0 | Lchr17 | 54550001-54750000 | 0 | 0 |
| 50 | 0 | 0 | Lchr10 | 32950001-33150000 | 0 | 0 |
| 51 | 0 | 0 | Gchr16 | 45650001-45950000 | 0 | 0 |
| 52 | 1 | 1 | Lchr20 | 42300001-42700000 | 1 | 1 |
| 53 | 0 | 1 | Gchr10 | 17900001-18200000 | 0 | 0 |
| 54 | 1.5 | 1.5 | Lchr13 | 18350001-18650000 | 1 | 1.5 |
| 55 | 1 | 0.49 | Gchr2 | 47750001-47850000 | 1 | 0.49 |
| 56 | 0 | 0 | Gchr2 | 64850001-64950000 | 0 | 0 |
| 57 | 0 | 0 | Gchr1 | 197450001-197750000 | 0 | 0 |
| 58 | 0 | 0 | Gchr2 | 133000001-133400000 | 0 | 0 |
| 59 | 0 | 0 | Lchr8 | 42950001-43350000 | 0 | 0 |
| 60 | 0 | 0 | Lchr2 | 230150001-230450000 | 0 | 0 |
| 61 | 1.5 | 1 | Lchr8 | 120750001-120950000 | 1 | 1 |
| 62 | 0 | 0 | Gchr13 | 69050001-69250000 | 0 | 0 |
| 63 | 0 | 0 | Lchr17 | 58350001-58550000 | 0 | 0 |
| 64 | 0 | 0 | Lchr2 | 47750001-47850000 | 0 | 0 |
| 65 | 0.49 | 1 | Gchr12 | 44300001-44400000 | 1 | 1 |
| 66 | 1 | 1 | Lchr12 | 109500001-109600000 | 1 | 1 |
| 67 | 0 | 0 | Lchr6 | 58450001-58550000 | 0 | 0 |
| 68 | 0 | 0 | Lchr1 | 219250001-219650000 | 0 | 0 |
| 69 | 1 | 0 | Lchr12 | 128050001-128650000 | 0 | 0 |
| 70 | 0 | 0 | Lchr20 | 42500001-42700000 | 0 | 0 |
| 71 | 0 | 0 | Gchr2 | 133050001-133350000 | 0 | 0 |
| 72 | 0.49 | 1.5 | Gchr7 | 86350001-86450000 | 1 | 1 |
| 73 | 0 | 0 | Lchr4 | 186800001-187200000 | 0 | 0 |
| 74 | 0 | 0 | Gchr20 | 39950001-40150000 | 0 | 0 |
| 75 | 0 | 0 | Lchr1 | 88850001-89450000 | 0 | 0 |
| 76 | 0 | 0 | Lchr12 | 127950001-128650000 | 0 | 0 |
| 77 | 0 | 0 | Lchr2 | 133000001-133400000 | 0 | 0 |
| 78 | 0 | 0 | Lchr7 | 86350001-86450000 | 0 | 0 |
| 79 | 0 | 0 | Lchr2 | 230250001-230450000 | 0 | 0 |
| 80 | 0 | 0 | Gchr12 | 127950001-128650000 | 0 | 0 |
| 81 | 0 | 0 | Lchr12 | 44300001-44400000 | 0 | 0 |
| 82 | 0 | 1 | Gchr8 | 42950001-43350000 | 0 | 0 |
| 83 | 1 | 1 | Gchr2 | 186650001-186750000 | 1 | 1 |
| 84 | 1.5 | 1.5 | Gchr17 | 61300001-61800000 | 1 | 1 |
| 85 | 0 | 0 | Lchr2 | 133050001-133350000 | 0 | 0 |
| 86 | 0 | 0.49 | Gchr12 | 109500001-109600000 | 0 | 0 |
| 87 | 0 | 0 | Lchr9 | 114800001-114900000 | 0 | 0 |
| 88 | 0 | 0 | Gchr6 | 58350001-58550000 | 0 | 0 |
| 89 | 0 | 0 | Lchr2 | 234200001-234700000 | 0 | 0 |
| 90 | 0 | 0 | Gchr8 | 120750001-121050000 | 0 | 0 |
| 91 | 0 | 0 | Gchr6 | 58400001-58600000 | 0 | 0 |
| 92 | 0 | 0 | Gchr8 | 67600001-67700000 | 0 | 0 |
| 93 | 0 | 0 | Lchr2 | 235800001-236100000 | 0 | 0 |
| 94 | 0 | 0 | Lchr7 | 69900001-70100000 | 0 | 0 |
| 95 | 0 | 1 | Gchr12 | 128050001-128650000 | 0 | 0 |
| 96 | 0 | 0 | Gchr16 | 75950001-76350000 | 0 | 0 |
| 97 | 1 | 1.5 | Gchr2 | 98700001-98900000 | 1 | 1 |
| 98 | 1 | 1.5 | Lchr12 | 95400001-95600000 | 1 | 1 |
| 99 | 0 | 0 | Lchr2 | 20200001-20500000 | 0 | 0 |
| 100 | 0 | 0 | Lchr13 | 21100001-21800000 | 0 | 0 |

TABLE 4

Final Selected Regions.

| # | Region | Start-Stop | Up/Down | Weight |
|---|---|---|---|---|
| 1 | Gchr8 | 43050001-43250000 | UP | 1.5 |
| 3 | Gchr1 | 212200001-212400000 | DOWN | 0.49 |
| 6 | Lchr17 | 58300001-58500000 | UP | 1.5 |
| 7 | Gchr15 | 61500001-61900000 | UP | 1 |
| 8 | Lchr1 | 148450001-148650000 | UP | 0.49 |
| 12 | Lchr10 | 17900001-18200000 | UP | 1.5 |
| 14 | Lchr9 | 88650001-88750000 | UP | 1.5 |
| 20 | Lchr10 | 89050001-89250000 | UP | 1 |
| 24 | Lchr10 | 27600001-27900000 | UP | 1 |
| 27 | Lchr13 | 21250001-21750000 | DOWN | 1 |
| 29 | Lchr16 | 67750001-67950000 | UP | 1 |
| 33 | Lchr13 | 21300001-21800000 | DOWN | 1 |
| 36 | Lchr10 | 27650001-27850000 | UP | 1 |
| 41 | Lchr4 | 186600001-187100000 | DOWN | 1 |
| 46 | Gchr6 | 58450001-58550000 | UP | 1 |
| 48 | Lchr20 | 57850001-58250000 | UP | 1 |
| 52 | Lchr20 | 42300001-42700000 | UP | 1 |
| 54 | Lchr13 | 18350001-18650000 | DOWN | 1.5 |
| 55 | Gchr2 | 47750001-47850000 | DOWN | 0.49 |
| 61 | Lchr8 | 120750001-120950000 | UP | 1 |
| 65 | Gchr12 | 44300001-44400000 | UP | 1 |
| 66 | Lchr12 | 109500001-109600000 | UP | 1 |
| 72 | Gchr7 | 86350001-86450000 | UP | 1 |
| 83 | Gchr2 | 186650001-186750000 | UP | 1 |
| 84 | Gchr17 | 61300001-61800000 | DOWN | 1 |
| 97 | Gchr2 | 98700001-98900000 | UP | 1 |
| 98 | Lchr12 | 95400001-95600000 | UP | 1 |

Gchr = global normalization/Lchr = local normalization

TABLE 5

Cross-Correlation Table.

| #deviant calls | Region1 | Region2 |
|---|---|---|
| 0 | 55 | 64 |
| 0 | 66 | 86 |
| 1 | 65 | 81 |
| 2 | 37 | 56 |
| 2 | 71 | 85 |
| 3 | 12 | 53 |
| 4 | 46 | 67 |
| 4 | 69 | 95 |
| 5 | 58 | 77 |
| 5 | 59 | 82 |
| 5 | 72 | 78 |
| 6 | 14 | 16 |
| 6 | 76 | 80 |
| 7 | 21 | 26 |
| 8 | 4 | 82 |
| 8 | 25 | 39 |
| 9 | 4 | 59 |
| 11 | 4 | 11 |
| 11 | 4 | 21 |
| 12 | 1 | 82 |
| 12 | 21 | 59 |
| 12 | 69 | 76 |
| 12 | 76 | 95 |
| 14 | 43 | 75 |
| 14 | 69 | 80 |
| 14 | 80 | 95 |

TABLE 5-continued

Cross-Correlation Table.

| #deviant calls | Region1 | Region2 |
|---|---|---|
| 15 | 1 | 11 |
| 15 | 1 | 59 |

1
2

TABLE 6

Performance Analysis

| Sample set size (#PrCa\|CNTRLS) | PrCa | CNTRLS | AUC | CI (95%) |
|---|---|---|---|---|
| 204\|207 | All | Normals | 0.927 | 0.902-0.951 |
| 89\|207 | Gleason < 7 | Normals | 0.954 | 0.929-0.978 |
| 84\|207 | Gleason ≥ 7 | Normals | 0.913 | 0.878-0.949 |
| 204\|227 | All | All + OMC | 0.927 | 0.902-0.951 |
| 89\|227 | Gleason < 7 | All + OMC | 0.954 | 0.929-0.978 |
| 84\|227 | Gleason ≥ 7 | All + OMC | 0.913 | 0.877-0.948 |
| 192\|201 | 41 ≤ Age ≤ 81* | 41 ≤ Age ≤ 81* | 0.920 | 0.893-0.946 |
| 76\|174 | 41 ≤ Age ≤ 65 | 41 ≤ Age ≤ 65 | 0.938 | 0.911-0.966 |
| 113\|118 | Sequence size: 40mer | Sequence size: 40mer | 0.907 | 0.871-0.943 |
| 91\|109 | Sequence size: 50mer | Sequence size: 50mer | 0.948 | 0.915-0.980 |

*Age range between youngest PrCa(41) and oldest control sample (81).

What is claimed is:

1. A method of analyzing circulating cell-free DNA in a sample from a patient that has or is suspected of having prostate cancer, comprising measuring, in a sample that is blood, serum or plasma, the level of
   a first cell-free DNA having a sequence at least 25 nucleotides in length unambiguously assigned to a first chromosomal region set forth in Table 4, and
   a second cell-free DNA having a sequence at least 25 nucleotides in length unambiguously assigned to a second chromosomal region set forth in Table 4 that is different from the first,
   wherein the sequences of said first and second cell-free DNAs are free of repetitive elements.

2. The method of claim 1, further comprising determining in said sample the level of a third cell free DNA having a sequence at least 25 nucleotides in length unambiguously assigned to a third chromosomal region set forth in Table 4, wherein said third chromosomal region is different from said first and second chromosomal regions, and the sequence of said third cell free DNA is free of repetitive elements.

3. The method of claim 1, further comprising measuring in said sample the level of at least 5, 8, 10, 15, or 20 additional different cell free DNAs, each having a sequence at least 25 nucleotides in length and free of repetitive elements, wherein each sequence is unambiguously assigned to a different chromosomal region set forth in Table 4.

4. The method of claim 1 further comprising effecting a prostate cancer therapy.

5. The method of claim 1, further comprising measuring the level of all cell-free DNAs in the sample that have a sequence at least 25 nucleotides in length free of repetitive elements unambiguously assigned to a chromosomal region listed in Table 4.

6. A method of treating a patient for prostate cancer, the method comprising:
   determining whether a human patient that has or is suspected of having prostate cancer, has a change in copy number of a chromosomal region set forth in Table 4 by:
      obtaining or having obtained a nucleic acid sample from blood, serum, or plasma from the patient and
      performing or having performed sequencing of nucleic acids obtained from the nucleic acid sample to determine copy number changes of chromosomal regions set forth in Table 4 by determining the level of a nucleic acid sequence of at least 25 nucleotides in length that is free of repetitive elements and unambiguously assigned to each of the chromosomal regions set forth in Table 4 and
   effecting a therapy for prostate cancer if the patient has:
      an increase in copy number of a sequence of at least 25 nucleotides in length unambiguously assigned to chromosome 8 region 43050001-43250000, chromosome 17 region 58300001-58500000, chromosome 15 region 61500001-61900000, chromosome 1 region 148450001-148650000, chromosome 10 region 17900001-18200000; chromosome 9 region 88650001-88750000, chromosome 10 89050001-89250000, chromosome 10 region 27650001-27850000, chromosome 6 region 58450001-58550000, chromosome 20 region 57850001-58250000, chromosome 20 region 42300001-42700000, chromosome 8 region 120750001-120950000, chromosome 12 region 44300001-44400000, chromosome 12 region 109500001-109600000, chromosome 7 region 86350001-86450000, chromosome 2 region 186650001-186750000, chromosome 2 region 98700001-98900000, or chromosome 12 region 95400001-95600000; or
   has a decrease in copy number of a sequence of at least 25 nucleotides in length unambiguously assigned to chromosome 1 region 212200001-212400000, chromosome 13 region 21250001-21750000, chromosome 13 region 21300001-21800000, chromosome 4 region 186600001-187100000, chromosome 13 region 18350001-18650000, chromosome 2 region 47750001-47850000, or chromosome 17 region 61300001-61800000.

* * * * *